(12) United States Patent
Hermiston et al.

(10) Patent No.: US 8,574,594 B2
(45) Date of Patent: *Nov. 5, 2013

(54) GENERATION OF REPLICATION COMPETENT VIRUSES FOR THERAPEUTIC USE

(75) Inventors: Terry Hermiston, Corte Madera, CA (US); Fang Jin, Danville, CA (US); Peter Kretschmer, San Francisco, CA (US)

(73) Assignee: PsiOxus Therapeutics Limited, London (GB)

( * ) Notice: Subject to any disclaimer, the term of this patent is extended or adjusted under 35 U.S.C. 154(b) by 637 days.

This patent is subject to a terminal disclaimer.

(21) Appl. No.: 12/488,627

(22) Filed: Jun. 22, 2009

(65) Prior Publication Data
US 2011/0217693 A1     Sep. 8, 2011

Related U.S. Application Data

(62) Division of application No. 11/288,821, filed on Nov. 28, 2005, now Pat. No. 7,550,296.

(60) Provisional application No. 60/632,671, filed on Dec. 1, 2004.

(51) Int. Cl.
*A61K 39/17* (2006.01)

(52) U.S. Cl.
USPC .................. 424/232.1; 424/214.1; 424/224.1; 424/229.1; 424/233.1; 536/23.1; 435/91.41; 435/473

(58) Field of Classification Search
None
See application file for complete search history.

(56) References Cited

U.S. PATENT DOCUMENTS

| | | | |
|---|---|---|---|
| 5,843,772 A | 12/1998 | Devine | |
| 6,240,524 B1 | 5/2001 | Suzuki | |
| 6,291,214 B1 | 9/2001 | Richards | |
| 6,420,524 B1 | 7/2002 | Craig | |
| 7,550,296 B2 | 6/2009 | Hermiston et al. | |
| 2002/0042137 A1 | 4/2002 | Richards | |
| 2009/0208924 A1 | 8/2009 | Hermiston | |

FOREIGN PATENT DOCUMENTS

WO   WO 98/37205   8/1998

OTHER PUBLICATIONS

Pending claims of U.S. Appl. No. 11/791,856 (20090208924), 6 pages, filed Feb. 1, 2001.
Babiss et al. "Deletion and Insertion Mutations in Early Region 1a of Type 5 Adenovirus That Produce Cold-Sensitive or Defective Phenotypes for Transformation," *Journal of Virology*, vol. 49, pp. 731-740, Mar. 1984.
Biery et al., "A simple in vitro Tn7-based transposition system with low target site selectivity for genome and gene analysis," *Nucl. Acids Res.* 28, 1067-77, Mar. 1, 2000.
Kirn and McCormick, "Replicating viruses as selective cancer therapeutics," *Molecular Medicine Today*, pp. 519-527, Dec. 1996.
Kretschmer et al., "Development of a transposon-based approach for identifying novel transgene insertion sites within the replicating adenovirus," *Mol. Therapy* 12, 118-27, Jul. 2005.
Luckow et al., "Efficient Generation of Infectious Recombinant Baculoviruses by Site-Specific Transposon-Mediated insertion of Foreign Genes into a Baculovirus Genome Propagated in *Escherichia coli*." *J. Virol.* (1993) 67: 4566-4579.
Richards et al., "The Admid System: Generation of Recombinant Adenovirusea by Tn7-Mediated Transposition in *E.coli*" *BioTechniques* vol. 29, No. 1: pp. 146-154 (2000).
Stellwagan et al., "Gain-of-Function Mutations in TnsC, an ATP-Dependent Transposition Protein That Activates the Bacterial Transposen Tn7" *Genetics*. (1997), 145: 573-585.
Arafat et al., "Effective single chain antibody (scFv) concentrations in vivo via adenoviral vector mediated expression of secretory scFv," *Gene Ther.* 9, 256-62, 2002.
Hermison & Kuhn, "Armed therapeutic viruses: Strategies and challenges to arming oncolytic viruses with therapeutic genes," *Cancer Gene Therapy* 9, 1022-35, Dec. 1, 2002.
Jin et al., "Identification of Novel Insertion Sites in the Ad5 Genome That Utilize the Ad Splicing Machinery for Therapeutic Gene Expression," *Mol. Therapy* 12, 1052-63, 2005.
Lee et al., "Replicating Adenoviral Vector-mediated Transfer of a Heatinducible Double Suicide Gene for Gene Therapy," *Cancer Gene Therapy* 8, 397-404, 2001.
Roshon et al., "Gene trap mutagenesis of hnRNP A2/B1: a cryptic 3' splice site in the neomycin resistance gene allows continued expression of the disrupted cellular gene," *BMC Genomics* 4, 1-11, 2003.
Boland et al., "Adenovirus-mediated Transfer of the Thyroid Sodium/Iodide Symporter Gene into Tumors for a Targeted Radiotherapy," *Cancer Res.* 60, 3484-92, 2000.
Cao et al., "The ORF RTL1 Transcript of Fowl Adenovirus Type-8 is Spliced and Truncated at Late Stages of the Virus Replication Cycle," *Virus Genes* 20, 135-37, 2000.
Kochanek et al., "A new adenoviral vector: Replacement of all viral coding sequences with 28 kb of DNA independently expressing both full-length dystrophin and β-galactosidase," *Proc. Natl. Acad. Sci. USA* 93, 5731-36, 1996.
Mizguchi et al., "Approaches for generating recombinant adenovirus vectors," *Advanced Drug Delivery Reviews* 52, 165-76, 2001.
Ugai et al., "Thermostability/Infectivity Defect Caused by Deletion of the Core Protein V Gene in Human Adenovirus Type 5 is Rescued by Thermo-selectable Mutations in the Core Protein X Precursor," *J. Mol. Biol.* 366, 1142-60, 2007.
Final Office Action mailed Sep. 28, 2011 in U.S. Appl. No. 11/791,856.
Pending claims in U.S. Appl. No. 11/791,856, filed Dec. 22, 2011.

*Primary Examiner* — Benjamin P Blumel
(74) *Attorney, Agent, or Firm* — Banner & Witcoff, Ltd.

(57) ABSTRACT

The present invention relates to the generation of replication-competent viruses having therapeutic utility. The replication-competent viruses of the invention can express proteins useful in the treatment of disease.

15 Claims, 9 Drawing Sheets

SEQUENCE LISTING

```
<160> NUMBER OF SEQ ID NOS: 22

<210> SEQ ID NO 1
<211> LENGTH: 26
<212> TYPE: DNA
<213> ORGANISM: Homo sapiens

<400> SEQUENCE: 1
tgctaatctt cctttctctc ttcagg                                    26

<210> SEQ ID NO 2
<211> LENGTH: 14
<212> TYPE: DNA
<213> ORGANISM: homo sapiens

<400> SEQUENCE: 2
tttctctctt cagg                                                 14

<210> SEQ ID NO 3
<211> LENGTH: 4
```

```
<212> TYPE: DNA
<213> ORGANISM: homo sapiens

<400> SEQUENCE: 3 cagg                                                                      4

<210> SEQ ID NO 4
<211> LENGTH: 39
<212> TYPE: DNA
<213> ORGANISM: artificial
<220> FEATURE:
<223> OTHER INFORMATION: oligonucleotide

<400> SEQUENCE: 4
aaatgtggcc ggccactgat tccacgtagt ggtcaggta                               39

<210> SEQ ID NO 5
<211> LENGTH: 43
<212> TYPE: DNA
<213> ORGANISM: artificial
<220> FEATURE:
<223> OTHER INFORMATION: oligonucleotide

<400> SEQUENCE: 5
ctagtacctg accactacgt ggaatcagtg gccggccaca ttt                          43

<210> SEQ ID NO 6
<211> LENGTH: 22
<212> TYPE: DNA
<213> ORGANISM: artificial
<220> FEATURE:
<223> OTHER INFORMATION: oligonucleotide

<400> SEQUENCE: 6
ggaattggcc ggccatatcc gc                                                 22

<210> SEQ ID NO 7
<211> LENGTH: 22
<212> TYPE: DNA
<213> ORGANISM: artificial
<220> FEATURE:
<223> OTHER INFORMATION: oligonucleotide

<400> SEQUENCE: 7
ggatatggcc ggccaattcc gc                                                 22

<210> SEQ ID NO 8
<211> LENGTH: 34
<212> TYPE: DNA
<213> ORGANISM: artificial
<220> FEATURE:
<223> OTHER INFORMATION: oligonucleotide

<400> SEQUENCE: 8
catggatggc cggccgctgt ggaatgtgtg tcag                                    34

<210> SEQ ID NO 9
<211> LENGTH: 42
<212> TYPE: DNA
<213> ORGANISM: artificial
<220> FEATURE:
<223> OTHER INFORMATION: oligonucleotide

<400> SEQUENCE: 9
tcagtagcta gccatggtgg ctaagagctg taattgaact gg                           42
```

<210> SEQ ID NO 10
<211> LENGTH: 25
<212> TYPE: DNA
<213> ORGANISM: artificial
<220> FEATURE:
<223> OTHER INFORMATION: oligonucleotide

<400> SEQUENCE: 10
cctttctctc ttcaggccgc catgg     25

<210> SEQ ID NO 11
<211> LENGTH: 32
<212> TYPE: DNA
<213> ORGANISM: artificial
<220> FEATURE:
<223> OTHER INFORMATION: oligonucleotide

<400> SEQUENCE: 11
gttctggatc cgtgagtcaa caggaaagtt cc     32

<210> SEQ ID NO 12
<211> LENGTH: 37
<212> TYPE: DNA
<213> ORGANISM: artificial
<220> FEATURE:
<223> OTHER INFORMATION: oligonucleotide

<400> SEQUENCE: 12
cctgctaatc ttcctttctc tcttcaggcc gccatgg     37

<210> SEQ ID NO 13
<211> LENGTH: 45
<212> TYPE: DNA
<213> ORGANISM: artificial
<220> FEATURE:
<223> OTHER INFORMATION: oligonucleotide

<400> SEQUENCE: 13
ctagccatgg cggcctgaag agagaaagga agattagcag gccgg     45

<210> SEQ ID NO 14
<211> LENGTH: 63
<212> TYPE: DNA
<213> ORGANISM: artificial
<220> FEATURE:
<223> OTHER INFORMATION: oligonucleotide

<400> SEQUENCE: 14
ccggcggcag aagatcccct cgttgcacag cttaaacagc gaggaggagc gcattttgcg     60
cta     63

<210> SEQ ID NO 15
<211> LENGTH: 27
<212> TYPE: DNA
<213> ORGANISM: artificial
<220> FEATURE:
<223> OTHER INFORMATION: primer

<400> SEQUENCE: 15
agctgtttaa accgatgtac gggccag     27

<210> SEQ ID NO 16
<211> LENGTH: 31
<212> TYPE: DNA
<213> ORGANISM: artificial
<220> FEATURE:
<223> OTHER INFORMATION: primer

```
<400> SEQUENCE: 16
tgacgtttaa actagaaggc acagtcgagg c                                     31

<210> SEQ ID NO 17
<211> LENGTH: 34
<212> TYPE: DNA
<213> ORGANISM: artificial
<220> FEATURE:
<223> OTHER INFORMATION: primer

<400> SEQUENCE: 17
ctagcgaatt cggtaccacg cgtctcgagg ccac                                  34

<210> SEQ ID NO 18
<211> LENGTH: 34
<212> TYPE: DNA
<213> ORGANISM: artificial
<220> FEATURE:
<223> OTHER INFORMATION: primer

<400> SEQUENCE: 18
catggtggcc tcgagacgcg tggtaccgaa ttcg                                  34

<210> SEQ ID NO 19
<211> LENGTH: 31
<212> TYPE: DNA
<213> ORGANISM: artificial
<220> FEATURE:
<223> OTHER INFORMATION: primer

<400> SEQUENCE: 19
ggccatggaa caggcagttt gccagtagtg c                                     31

<210> SEQ ID NO 20
<211> LENGTH: 45
<212> TYPE: DNA
<213> ORGANISM: artificial
<220> FEATURE:
<223> OTHER INFORMATION: primer

<400> SEQUENCE: 20
ctaatacgac tcactatagg gcaagcagtg gtatcaacgc agagt                      45

<210> SEQ ID NO 21
<211> LENGTH: 21
<212> TYPE: DNA
<213> ORGANISM: artificial
<220> FEATURE:
<223> OTHER INFORMATION: primer

<400> SEQUENCE: 21
taatacgact cactataggg c                                                21

<210> SEQ ID NO 22
<211> LENGTH: 32325
<212> TYPE: DNA
<213> ORGANISM: Adenovirus

<400> SEQUENCE: 22
ctatctatat aatatacctt atagatggaa tggtgccaat atgtaaatga ggtgatttta      60
aaaagtgtgg atcgtgtggt gattggctgt ggggttaacg ctaaaaggg  gcggtgcgac    120 cgtgggaaaa tgacgttttg tggggtgga gttttttttgc aagttgtcgc gggaaatgtg    180
acgcataaaa aggcttttttt ctcacggaac tacttagttt tcccacggta tttaacagga   240
```

```
aatgaggtag ttttgaccgg atgcaagtga aaattgttga ttttcgcgcg aaaactgaat      300
gaggaagtgt ttttctgaat aatgtggtat ttatggcagg gtggagtatt tgttcagggc      360
caggtagact ttgacccatt acgtggaggt ttcgattacc gtgtttttta cctgaatttc      420
cgcgtaccgt gtcaaagtct tctgttttta cgtaggtgtc agctgatcgc tagggtattt      480
atacctcagg gtttgtgtca agaggccact cttgagtgcc agcgagaaga gttttctcct      540
ctgcgccggc agtttaataa taaaaaaatg agagatttgc gatttctgcc tcaggaaata      600
atctctgctg agactggaaa tgaaatattg gagcttgtgg tgcacgccct gatgggagac      660
gatccggagc cacctgtgca gcttttttgag cctcctacgc ttcaggaact gtatgattta      720
gaggtagagg gatcggagga ttctaatgag gaagctgtaa atggctttt taccgattct      780
atgcttttag ctgctaatga agggttagaa ttagatccgc ctttggacac ttttgatact      840
ccaggggtaa ttgtgaaaag cggtacaggt gtaagaaaat tacctgattt gagttccgtg      900
gactgtgatt tgcactgcta tgaagacggg tttcctccga gtgatgagga ggaccatgaa      960
aaggagcagt ccatgcagac tgcagcgggt gagggagtga aggctgccaa tgttggtttt     1020
cagttggatt gcccggagct tcctggacat ggctgtaagt cttgtgaatt tcacaggaaa     1080
aatactggag taaaggaact gttatgttcg cttttgttata tgagaacgca ctgccacttt     1140
atttacagta agtgtgttta agttaaaatt taaaggaata tgctgttttt cacatgtata     1200
ttgagtgtga gttttgtgct tcttattata ggtcctgtgt ctgatgctga tgaatcacca     1260
tctcctgatt ctactacctc acctcctgag attcaagcac ctgttcctgt ggacgtgcgc     1320
aagcccattc ctgtgaagct taagcctggg aaacgtccag cagtggaaaa acttgaggac     1380
ttgttacagg gtggggacgg acctttggac ttgagtacac ggaaacgtcc aagacaataa     1440
gtgttccata tccgtgttta cttaaggtga cgtcaatatt tgtgtgacag tgcaatgtaa     1500
taaaaatatg ttaactgttc actggttttt attgcttttt gggcgggac tcaggtatat      1560
aagtagaagc agacctgtgt ggttagctca taggagctgg cttcatcca tggaggtttg      1620
ggccattttg gaagacctta ggaagactag gcaactgtta gagaacgctt cggacggagt     1680
ctccggtttt tggagattct ggttcgctag tgaattagct agggtagttt ttaggataaa     1740
acaggactat aaacaagaat ttgaaaagtt gttggtagat tgcccaggac ttttgaagc      1800
tcttaatttg ggccatcagg ttcactttaa agaaaagtt ttatcagttt tagacttttc     1860
aaccccaggt agaactgctg ctgctgtggc ttttcttact tttatattag ataaatggat     1920
cccgcagact catttcagca ggggatacgt tttggatttc atagccacag cattgtggag     1980
aacatggaag gttcgcaaga tgaggacaat cttaggttac tggccagtgc agcctttggg     2040
tgtagcggga atcctgaggc atccaccggt catgccagcg gttctggagg aggaacagca     2100
agaggacaac ccgagagccg gcctggaccc tccagtggag gaggcggagt agctgacttg     2160
tctcctgaac tgcaacgggt gcttactgga tctacgtcca ctggacggga taggggcgtt     2220
aagagggaga gggcatctag tggtactgat gctagatctg agttggcttt aagtttaatg     2280
agtcgcagac gtcctgaaac catttggtgg catgaggttc agaaagaggg aagggatgaa     2340
gtttctgtat tgcaggagaa atattcactg gaacaggtga aaacatgttg gttggagcct     2400
gaggatgatt gggaggtggc cattaaaaat tatgccaaga tagctttgag gcctgataaa     2460
cagtataaga ttactagacg gattaatatc cggaatgctt gttacatatc tggaaatggg     2520
gctgaggtgg taatagatac tcaagacaag gcagttatta gatgctgcat gatggatatg     2580
tggcctgggg tagtcggtat ggaagcagta acttttgtaa atgttaagtt tagggagat     2640
```

```
ggttataatg gaatagtgtt tatggccaat accaaactta tattgcatgg ttgtagcttt    2700
tttggtttca acaatacctg tgtagatgcc tggggacagg ttagtgtacg gggatgtagt    2760
ttctatgcgt gttggattgc cacagctggc agaaccaaga gtcaattgtc tctgaagaaa    2820
tgcatatttc aaagatgtaa cctgggcatt ctgaatgaag gcgaagcaag gtccgccac     2880 tgcgcttcta cagatactgg atgttttatt ttgattaagg gaaatgccag cgtaaagcat    2940
aacatgattt gcggtgcttc cgatgagagg cctttatcaaa tgctcacttg tgctggtggg   3000
cattgtaata tgctggctac tgtgcatatt gtttcccatc aacgcaaaaa atggcctgtt    3060
tttgatcaca atgtgatgac gaagtgtacc atgcatgcag gtgggcgtag aggaatgttt   3120
atgccttacc agtgtaacat gaatcatgtg aaagtgttgt tggaaccaga tgccttttcc   3180
agaatgagcc taacaggaat ttttgacatg aacatgcaaa tctggaagat cctgaggtat   3240
gatgatacga gatcgagggt acgcgcatgc gaatgcggag gcaagcatgc caggttccag    3300
ccggtgtgtg tagatgtgac tgaagatctc agaccggatc atttggttat tgcccgcact   3360
ggagcagagt tcggatccag tggagaagaa actgactaag gtgagtattg gaaaactttt    3420
ggggtgggat tttcagatgg acagattgag taaaaatttg ttttttctgt cttgcagctg   3480
tcatgagtgg aaacgcttct tttaaggggg gagtcttcag cccttatctg acagggcgtc   3540
tcccatcctg gcaggagtt cgtcagaatg ttatgggatc tactgtggat ggaagacccg   3600
tccaacccgc caattcttca acgctgacct atgctacttt aagttcttca cctttggacg   3660
cagctgcagc tgccgccgcc gcttctgttg ccgctaacac tgtgcttgga atgggttact   3720
atggaagcat catggctaat tccacttcct ctaataaccc ttctaccctg actcaggaca   3780
agttacttgt ccttttggcc cagctggagg ctttgaccca acgtctgggt gaactttctc   3840
agcaggtggt cgagttgcga gtacaaactg agtctgctgt cggcacggca aagtctaaat   3900
aaaaaaatcc cagaatcaat gaataaataa acaagcttgt tgttgattta aaatcaagtg   3960
tttttatttc attttttcgcg cacggtatgc cctagaccac cgatctctat cattgagaac   4020
tcggtggatt ttttccagga tcctatagag gtgggattga atgtttagat acatgggcat   4080
taggccgtct ttggggtgga gatagctcca ttgaagggat tcatgctccg gggtagtgtt   4140
gtaaatcacc cagtcataac aaggtcgcag tgcatggtgt tgcacaatat cttttagaag   4200
taggctgatt gccacagata agcccttggt gtaggtgttt acaaaccggt tgagctggga   4260
tgggtgcatt cggggtgaaa ttatgtgcat ttttggattgg attttttaagt tggcaatatt   4320 gccgccaaga tcccgtcttg ggttcatgtt atgaaggacc accaagacgg tgtatccggt   4380
acatttagga aatttatcgt gcagcttgga tggaaaagcg tggaaaaatt tggagacacc   4440
cttgtgtcct ccaagatttt ccatgcactc atccatgata atagcaatgg ggccgtgggc   4500
agcggcgcgg gcaaacacgt tccgtgggtc tgacacatca tagttatgtt cctgagttaa   4560
atcatcataa gccattttaa tgaatttggg gcggagagta ccagattggg gtatgaatgt   4620
tccttcgggc cccggagcat agttcccctc acagatttgc atttcccaag ctttcagttc   4680
cgagggtgga atcatgtcca cctggggggc tatgaaaaac accgtttctg gggcgggggt   4740
gattaattgt gatgatagca aatttctgag caattgagat ttgccacatc cggtggggcc   4800
ataaatgatt ccgattacgg gttgcaggtg gtagtttagg gaacggcaac tgccgtcttc   4860
tcgaagcaag ggggccacct cgttcatcat ttcccttaca tgcatatttt cccgcaccaa   4920
atccattagg aggcgctctc ctcctagtga tagaagttct tgtagtgagg aaaagttttt   4980
cagcggtttc agaccgtcag ccatgggcat tttggagaga gtttgctgca aaagttctag   5040
```

```
tctgttccac agttcagtga tgtgttctat ggcatctcga tccagcagac ctcctcgttt    5100
cgcgggtttg gacggctcct ggaatagggt atgagacgat gggcgtccag cgctgccagg    5160
gttcggtcct tccagggtct cagtgttcga gtcaggttg tttccgtcac agtgaagggg     5220
tgtgcgcctg cttgggcgct tgccagggtg cgcttcagac tcatcctgct ggtcgaaaac    5280
ttctgtcgct tggcgccctg tatgtcggcc aagtagcagt ttaccatgag ttcgtagttg    5340
agcgcctcgg ctgcgtggcc tttggcgcgg agcttacctt tggaagtttt cttgcatacc    5400
gggcagtata ggcatttcag cgcatacaac ttgggcgcaa ggaaaacgga ttctggggag    5460
tatgcatctg cgccgcagga ggcgcaaaca gtttcacatt ccaccagcca ggttaaatcc    5520
ggttcattgg ggtcaaaaac aagttttccg ccatatttt tgatgcgttt cttacctttg     5580
gtctccatga gttcgtgtcc tcgttgagtg acaaacaggc tgtccgtgtc cccgtagact    5640
gattttacag gcctcttctc cagtggagtg cctcggtctt cttcgtacag gaactctgac    5700
cactctgata caaaggcgcg cgtccaggcc agcacaaagg aggctatgtg ggaggggtag    5760
cgatcgttgt caaccagggg gtccacccttt tccaaagtat gcaaacacat gtcaccctct   5820
tcaacatcca ggaatgtgat tggcttgtag gtgtatttca cgtgacctgg ggtccccgct    5880
gggggggtat aaaagggggc ggttctttgc tcttcctcac tgtcttccgg atcgctgtcc    5940
aggaacgtca gctgttgggg taggtattcc ctctcgaagg cgggcatgac ctctgcactc    6000
aggttgtcag tttctaagaa cgaggaggat ttgatattga cagtgccggt tgagatgcct    6060
ttcatgaggt tttcgtccat ctggtcagaa aacacaattt ttttattgtc aagtttggtg    6120
gcaaatgatc catacagggc gttggataaa agtttggcaa tggatcgcat ggtttggttc    6180
ttttccttgt ccgcgcgctc tttggcgcg atgttgagtt ggacatactc gcgtgccagg     6240
cacttccatt cggggaagat agttgttaat tcatctggca cgattctcac ttgccaccct    6300
cgattatgca aggtaattaa atccacactg gtggccacct cgcctcgaag gggttcattg    6360
gtccaacaga gcctacctcc tttcctagaa cagaaagggg gaagtgggtc tagcataagt    6420
tcatcgggag ggtctgcatc catggtaaag attcccggaa gtaaatcctt atcaaaatag    6480
ctgatgggag tggggtcatc taaggccatt tgccattctc gagctgccag tgcgcgctca    6540
tatgggttaa ggggactgcc ccatggcatg ggatgggtga gtgcagaggc atacatgcca    6600
cagatgtcat agacgtagat gggatcctca agatgcctta tgtaggttgg atagcatcgc    6660 cccctctga tacttgctcg cacatagtca tatagttcat gtgatggcgc tagcagcccc     6720
ggacccaagt tggtgcgatt gggttttct gttctgtaga cgatctggcg aaagatggcg     6780
tgagaattgg aagagatggt gggtctttga aaaatgttga atgggcatg aggtagacct     6840 acagagtctc tgacaaagtg ggcataagat tcttgaagct tggttaccag ttcggcggtg    6900
acaagtacgt ctagggcgca gtagtcaagt gtttcttgaa tgatgtcata acctggttgg    6960
tttttctttt cccacagttc gcggttgaga aggtattctt cgcgatcctt ccagtactct    7020
tctagcggaa accgtctttt gtctgcacgg taagatccta gcatgtagaa ctgattaact    7080
gccttgtaag ggcagcagcc cttctctacg ggtagagagt atgcttgagc agcttttcgt    7140
agcgaagcgt gagtaagggc aaaggtgtct ctgaccatga ctttgaggaa ttggtatttg    7200
aagtcgatgt cgtcacaggc tccctgttcc cagagttgga agtctacccg tttcttgtag    7260
gcggggttgg gcaaagcgaa agtaacatca ttgaagagaa tcttgccggc cctgggcatg    7320
aaattgcgag tgatgcgaaa aggctgtggt acttccgctc ggttattgat aacctgggca    7380
gctaggacga tctcgtcgaa accgttgatg ttgtgtccta cgatgtataa ttctatgaaa    7440
```

```
cgcggcgtgc ctctgacgtg aggtagctta ctgagctcat caaaggttag gtctgtgggg    7500
tcagataagg cgtagtgttc gagagcccat tcgtgcaggt gaggattcgc tttaaggaag    7560
gaggaccaga ggtccactgc cagtgctgtt tgtaactggt cccggtactg acgaaaatgc    7620
cgtccgactg ccatttttc tggggtgacg caatagaagg tttggggtc ctgccgccag      7680 cgatcccact tgagttttat ggcgaggtca taggcgatgt tgacgagccg ctggtctcca    7740
gagagtttca tgaccagcat gaaggggatt agctgcttgc caaaggaccc catccaggtg    7800 taggttttcca catcgtaggt gagaaagagc ctttctgtgc gaggatgaga gccaatcggg   7860
aagaactgga tctcctgcca ccagttggag gaatggctgt tgatgtgatg gaagtagaac   7920
tccctgcgac gcgccgagca ttcatgcttg tgcttgtaca gacggccgca gtagtcgcag   7980
cgttgcacgg gttgtatctc gtgaatgagt tgtacctggc ttcccttgac gagaaatttc   8040
agtgggaagc cgaggcctgg cgattgtatc tcgtgcttta ctatgttgtc tgcatcggcc   8100
tgttcatctt ctgtctcgat ggtggtcatg ctgacgagcc ctcgcgggag gcaagtccag   8160
acctcggcgc ggcaggggcg gagctcgagg acgagagcgc gcaggctgga gctgtccagg   8220
gtcctgagac gctgcggact caggttagta ggcagtgtca ggagattaac ttgcatgatc   8280
ttttggaggg cgtgcgggag gttcagatag tacttgatct caacgggtcc gttggtggag   8340
atgtcgatgg cttgcaggqt tccgtgtccc ttggcgcta ccaccgtgcc cttgttttc     8400 attttggacg gcggtggctc tgttgcttct tgcatgttta aagcggtgt cgagggcgcg    8460 caccgggcgc caggggcggc tcgggacccg gcggcatggc tggcagtggt acgtcggcgc   8520
cgcgcgcggg taggttctgg tactgcgccc tgagaagact cgcatgcgcg acgacgcggc   8580
ggttgacatc ctggatctga cgcctctggg tgaaagctac cggccccgtg agcttgaacc   8640
tgaaagagag ttcaacagaa tcaatctcgg tatcgttgac ggcggcttgc ctaaggattt   8700
cttgcacgtc accagagttg tcctggtagg cgatctccgc catgaactgc tcgatctctt   8760
cctcttgaag atctccgcgg cccgctctct cgacggtggc cgcgaggtcg ttggagatgc   8820
gcccaatgag ttgagagaat gcattcatgc ccgcctcgtt ccagacgcgg ctgtagacca   8880
cggcccccac gggatctctc gcgcgcatga ccacctgggc gaggttgagc tccacgtggc   8940
gggtgaagac cgcatagttg cataggcgct ggaaaaggta gttgagtgtg gtggcgatgt   9000
gctcggtgac gaagaaatac atgatccatc gtctcagcgg catctcgctg acatcgccca   9060
gagcttccaa gcgctccatg gcctcgtaga agtccacggc aaaattaaaa aactgggagt   9120
ttcgcgcgga cacggtcaac tcctcttcca gaagacggat aagttcggcg atggtggtgc   9180
gcacctcgcg ctcgaaagcc cctgggattt cttcctcaat ctcttcttct tccactaaca   9240
tctcttcctc ttcaggtggg gctgcaggag gaggggaac gcggcgacgc cggcggcgca    9300
cgggcagacg tcgatgaat cttcaatga cctctccgcg gcggcggcgc atggtttcag    9360
tgacggcgcg gccgttctcg cgcggtcgca gagtaaaaac accgccgcgc atctccttaa   9420
agtggtgact gggaggttct ccgtttggga gggagagggc gctgattata cattttatta   9480
attggcccgt agggactgca cgcagagatc tgatcgtgtc aagatccacg ggatctgaaa   9540
acctttcgac gaaagcgtct aaccagtcac agtcacaagg taggctgagt acggcttctt   9600
gtgggcgggg gtggttatgt gttcggtctg ggtcttctgt ttcttcttca tctcgggaag   9660
gtgagacgat gctgctggtg atgaaattaa agtaggcagt tctaagacgg cggatggtgg   9720
cgaggagcac caggtctttg ggtccggctt gctggatacg caggcgattg gccattcccc   9780
aagcattatc ctgacatcta gcaagatctt tgtagtagtc ttgcatgagc cgttctacgg   9840
```

-continued

```
gcacttcttc ctcacccgtt ctgccatgca tacgtgtgag tccaaatccg cgcattggtt   9900
gtaccagtgc caagtcagct acgactcttt cggcgaggat ggcttgctgt acttgggtaa   9960
gggtggcttg aaagtcatca aaatccacaa agcggtggta agctcctgta ttaatggtgt  10020
aagcacagtt ggccatgact gaccagttaa ctgtctggtg accagggcgc acgagctcgg  10080
tgtatttaag gcgcgaatag gcgcgggtgt caaagatgta atcgttgcag gtgcgcacca  10140
gatactggta ccctataaga aaatgcggcg gtggttggcg gtagagaggc catcgttctg  10200
tagctggagc gccaggggcg aggtcttcca acataaggcg gtgatagccg tagatgtacc  10260
tggacatcca ggtgattcct gcggcggtag tagaagcccg aggaaactcg cgtacgcggt  10320
tccaaatgtt gcgtagcggc atgaagtagt tcattgtagg cacggtttga ccagtgaggc  10380
gcgcgcagtc attgatgctc tatagacacg gagaaaatga aagcgttcag cgactcgact  10440
ccgtagcctg gaggaacgtg aacgggttgg gtcgcggtgt accccggttc gagacttgta  10500
ctcgagccgg ccggagccgc ggctaacgtg gtattggcac tcccgtctcg acccagccta  10560
caaaaatcca ggatacggaa tcgagtcgtt ttgctggttt ccgaatggca gggaagtgag  10620
tcctattttt tttttttgcc gctcagatgc atcccgtgct gcgacagatg cgcccccaac  10680
aacagccccc ctcgcagcag cagcagcagc aatcacaaaa ggctgtccct gcaactactg  10740
caactgccgc cgtgagcggt gcgggacagc ccgcctatga tctggacttg gaagagggcg  10800
aaggactggc acgtctaggt gcgccttcac ccgagcggca tccgcgagtt caactgaaaa  10860
aagattctcg cgaggcgtat gtgccccaac agaacctatt tagagacaga agcggcgagg  10920
agccggagga gatgcgagct tcccgcttta acgcgggtcg tgagctgcgt cacggtttgg  10980
accgaagacg agtgttgcgg gacgaggatt tcgaagttga tgaaatgaca gggatcagtc  11040
ctgccagggc acacgtggct gcagccaacc ttgtatcggc ttacgagcag acagtaaagg  11100
aagagcgtaa cttccaaaag tcttttaata atcatgtgcg aaccctgatt gcccgcgaag  11160
aagttaccct tggtttgatg catttgtggg atttgatgga agctatcatt cagaacccta  11220
ctagcaaacc tctgaccgcc cagctgtttc tggtggtgca acacagcaga gacaatgagg  11280
ctttcagaga ggcgctgctg aacatcaccg aacccgaggg gagatggttg tatgatctta  11340
tcaacattct acagagtatc atagtgcagg agcggagcct gggcctggcc gagaaggtgg  11400
ctgccatcaa ttactcggtt ttgagcttgg gaaaatatta cgctcgcaaa atctacaaga  11460
ctccatacgt tcccatagac aaggaggtga agatagatgg gttctacatg cgcatgacgc  11520
tcaaggtctt gaccctgagc gatgatcttg ggtgtatcg caatgacaga atgcatcgcg  11580
cggttagcgc cagcaggagg cgcgagttaa gcgacaggga actgatgcac agtttgcaaa  11640
gagctctgac tggagctgga accgagggtg agaattactt cgacatggga gctgacttgc  11700
agtggcagcc tagtcgcagg gctctgagcg ccgcgacggc aggatgtgag cttccttaca  11760
tagaagaggc ggatgaaggc gaggaggaag agggcgagta cttggaagac tgatggcaca  11820
acccgtgttt tttgctagat ggaacagcaa gcaccggatc ccgcaatgcg ggcggcgctg  11880
cagagccagc cgtccggcat taactcctcg gacgattgga cccaggccat gcaacgtatc  11940
atggcgttga cgactcgcaa ccccgaagcc tttagacagc aaccccaggc caaccgtcta  12000
tcggccatca tggaagctgt agtgccttcc cgctctaatc ccactcatga gaaggtcctg  12060
gccatcgtga acgcgttggt ggagaacaaa gctattcgtc cagatgaggc cggactggta  12120
tacaacgctc tcttagaacg cgtggctcgc tacaacagta gcaatgtgca aaccaatttg  12180
gaccgtatga taacagatgt acgcgaagcc gtgtctcagc gcgaaaggtt ccagcgtgat  12240
```

```
gccaacctgg gttcgctggt ggcgttaaat gctttcttga gtactcagcc tgctaatgtg   12300
ccgcgtggtc aacaggatta tactaacttt ttaagtgctt tgagactgat ggtatcagaa   12360
gtacctcaga gcgaagtgta tcagtccggt cctgattact tctttcagac tagcagacag   12420
ggcttgcaga cggtaaatct gagccaagct tttaaaaacc tttaaaggtt tgtggggagt   12480
gcatgccccg gtaggagaaa gagcaaccgt gtctagcttg ttaactccga actcccgcct   12540
attattactg ttggtagctc cttttcaccga cagcggtagc atcgaccgta attcctattt   12600
gggttaccta ctaaacctgt atcgcgaagc catagggcaa agtcaggtgg acgagcagac   12660
ctatcaagaa attacccaag tcagtcgcgc tttgggacag aagacactg gcagtttgga    12720 agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca gcgcgaaata tggagcccag   12900
catgtatgcc agtaaccgac cttttcattaa caaactgctg gactacttgc acagagctgc   12960
cgctatgaac tctgattatt tcaccaatgc catcttaaac ccgcactggc tgcccccacc   13020
tggtttctac acgggcgaat atgacatgcc cgacctaat gacggatttc tgtgggacga    13080
cgtggacagc gatgtttttt cacctctttc tgatcatcgc acgtggaaaa aggaaggcgg   13140
cgatagaatg cattcttctg catcgctgtc cggggtcatg ggtgctaccg cggctgagcc   13200
cgagtctgca agtcctttc ctagtctacc cttttctcta cacagtgtac gtagcagcga    13260
agtgggtaga ataagtcgcc cgagtttaat gggcgaagag gagtatctaa cgattcctt    13320 gctcagaccg gcaagagaaa aaaatttccc aaacaatgga atagaaagtt tggtggataa   13380
aatgagtaga tggaagactt atgctcagga tcacagagac gagcctggga tcatggggat   13440
tacaagtaga gcgagccgta gacgccagcg ccatgacaga cagaggggtc ttgtgtggga   13500
cgatgaggat tcgccgatg atagcagcgt gctggacttg ggtgggagag gaaggggcaa    13560
cccgtttgct catttgcgcc ctcgcttggg tggtatgttg taaaaaaaaa taaaaaaaaa   13620
actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800
cctttgtgcc tccgcgatac ctggcaccta cggagggcag aaacagcatt cgttattcgg   13860
aactggcacc tcagtacgat accaccaggt tgtatctggt ggacaacaag tcggcggaca   13920
ttgcttctct gaactatcag aatgaccaca gcaacttctt gaccacggtg gtgcaaaaca   13980
atgactttac ccctacggaa gccagcaccc agaccattaa ctttgatgaa cgatcgcggt   14040
ggggcggtca gctaaagacc atcatgcata ctaacatgcc aaacgtgaac gagtatatgt   14100
ttagtaacaa gttcaaagcg cgtgtgatgg tgtccagaaa acctcccgac ggtgctgcag   14160
ttggggatac ttatgatcac aagcaggata ttttgaaata tgagtggttc gagtttactt   14220
tgccagaagg caacttttca gttactatga ctattgattt tgatgaacaat gccatcatag   14280 ataattactt gaaagtgggt agacagaatg gagtgcttga aagtgacatt ggtgttaagt   14340
tcgacaccag gaacttcaag ctgggatggg atcccgaaac caagttgatc atgcctggag   14400
tgtatacgta tgaagccttc catcctgaca ttgtcttact gcctggctgc ggagtggatt   14460
ttaccgagag tcgtttgagc aaccttcttg gtatcagaaa aaaacagcca tttcaagagg   14520
gttttaagat tttgtatgaa gatttagaag gtggtaatat tccggccctc ttggatgtag   14580
atgcctatga gaacagtaag aaagaacaaa aagccaaaat agaagctgct acagctgctg   14640
```

```
cagaagctaa ggcaaacata gttgccagcg actctacaag ggttgctaac gctggagagg   14700
tcagaggaga caattttgcg ccaacacctg ttccgactgc agaatcatta ttggccgatg   14760
tgtctgaagg aacggacgtg aaactcacta ttcaacctgt agaaaaagat agtaagaata   14820
gaagctataa tgtgttggaa gacaaaatca acacagccta tcgcagttgg tatctttcgt   14880
acaattatgg cgatcccgaa aaaggagtgc gttcctggac attgctcacc acctcagatg   14940
tcacctgcgg agcagagcag gtctactggt cgcttccaga catgatgaag gatcctgtca   15000
ctttccgctc cactagacaa gtcagtaact accctgtggt gggtgcagag cttatgcccg   15060
tcttctcaaa gagcttctac aacgaacaag ctgtgtactc ccagcagctc cgccagtcca   15120
cctcgcttac gcacgtcttc aaccgctttc ctgagaacca gattttaatc cgtccgccgg   15180
cgcccaccat taccaccgtc agtgaaaacg ttcctgctct cacagatcac gggaccctgc   15240
cgttgcgcag cagtatccgg ggagtccaac gtgtgaccgt tactgacgcc agacgccgca   15300
cctgtcccta cgtgtacaag gcactgggca tagtcgcacc gcgcgtcctt tcaagccgca   15360
ctttctaaaa aaaaaaaaaa tgtccattct tatctcgccc agtaataaca ccggttgggg   15420
tctgcgcgct ccaagcaaga tgtacggagg cgcacgcaaa cgttctaccc aacatcctgt   15480
ccgtgttcgc ggacattttc gcgctccatg gggcgccctc aagggccgca ctcgcgttcg   15540
aaccaccgtc gatgatgtaa tcgatcaggt ggttgccgac gcccgtaatt atactcctac   15600
tgcgcctaca tctactgtgg atgcagttat tgacagtgta gtggctgacg ctcgcaacta   15660
tgctcgacgt aagagccggc gaaggcgcat tgccagacgc caccgagcta ccactgccat   15720
gcgagccgca agagctctgc tacgaagagc tagacgcgtg gggcgaagag ccatgcttag   15780
ggcggccaga cgtgcagctt cgggcgccag cgccggcagg tcccgcaggc aagcagccgc   15840
tgtcgcagcg gcgactattg ccgacatggc ccaatcgcga agaggcaatg tatactgggt   15900
gcgtgacgct gccaccggtc aacgtgtacc cgtgcgcacc cgtcccccctc gcacttagaa   15960 gatactgagc agtctccgat gttgtgtccc agcggcgagg atgtccaagc gcaaatacaa   16020
ggaagaaatg ctgcaggtta tcgcacctga agtctacggc caaccgttga aggatgaaaa   16080 aaaacccgc aaaatcaagc gggttaaaaa ggacaaaaaa gaagaggaag atggcgatga   16140
tgggctggcg gagtttgtgc gcgagtttgc cccacggcga cgcgtgcaat ggcgtgggcg   16200
caaagttcga catgtgttga gacctggaac ttcggtggtc tttacacccg gcgagcgttc   16260
aagcgctact tttaagcgtt cctatgatga ggtgtacggg gatgatgata ttcttgagca   16320
ggcggctgac cgattaggcg agtttgctta tggcaagcgt agtagaataa cttccaagga   16380
tgagacagtg tcgatacccct tggatcatgg aaatcccacc cctagtctta aaccggtcac   16440
tttgcagcaa gtgttacccg taactccgcg aacaggtgtt aaacgcgaag gtgaagattt   16500
gtatcccact atgcaactga tggtacccaa acgccagaag ttggaggacg ttttggagaa   16560
agtaaaagtg gatccagata ttcaacctga ggttaaagtg agacccatta agcaggtagc   16620
gcctggtctg ggggtacaaa ctgtagacat taagattccc actgaaagta tggaagtgca   16680
aactgaaccc gcaaagccta ctgccacctc cactgaagtg caaacggatc catggatgcc   16740
catgcctatt acaactgacg ccgccggtcc cactcgaaga tcccgacgaa agtacggtcc   16800
agcaagtctg ttgatgccca attatgttgt acacccatct attattccta ctcctggtta   16860
ccgaggcact cgctactatc gcagccgaaa cagtacctcc cgccgtcgcc gcaagacacc   16920
tgcaaatcgc agtcgtcgcc gtagacgcac aagcaaaccg actcccggcg ccctggtgcg   16980
gcaagtgtac cgcaatggta gtgcggaacc tttgacactg ccgcgtgcgc gttaccatcc   17040
```

```
gagtatcatc acttaatcaa tgttgccgct gcctccttgc agatatggcc ctcacttgtc   17100
gccttcgcgt tcccatcact ggttaccgag gaagaaactc gcgccgtaga agagggatgt   17160
tgggacgcgg aatgcgacgc tacaggcgac ggcgtgctat ccgcaagcaa ttgcggggtg   17220
gttttttacc agccttaatt ccaattatcg ctgctgcaat tggcgcgata ccaggcatag   17280
cttccgtggc ggttcaggcc tcgcaacgac attgacattg aaaaaaacg tataaataaa    17340 aaaaaaaaaa tacaatggac tctgacactc ctggtcctgt gactatgttt tcttagagat   17400
ggaagacatc aatttttcat ccttggctcc gcgacacggc acgaagccgt acatgggcac   17460
ctggagcgac atcggcacga gccaactgaa cgggggcgcc ttcaattgga gcagtatctg   17520
gagcgggctt aaaaattttg gctcaaccat aaaaacatac gggaacaaag cttggaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaacccca ggtgaaatgc aagtggagga   17760
agaaattcct ccgccagaaa aacgaggcga caagcgtccg cgtcccgatt tggaagagac   17820
gctggtgacg cgcgtagatg aaccgccttc ttatgaggaa gcaacgaagc ttggaatgcc   17880
caccactaga ccgatagccc caatggccac cggggtgatg aaaccttctc agttgcatcg   17940
acccgtcacc ttgatttgc ccctcccc tgctgctact gctgtacccg cttctaagcc       18000
tgtcgctgcc ccgaaaccag tcgccgtagc caggtcacgt cccggggcg ctcctcgtcc    18060 aaatgcgcac tggcaaaata ctctgaacag catcgtgggt ctaggcgtgc aaagtgtaaa   18120
acgccgtcgc tgcttttaat taaatatgga gtagcgctta acttgcctat ctgtgtatat   18180
gtgtcattac acgccgtcac agcagcgag gaaaaagga agaggtcgtg cgtcgacgct    18240
gagttacttt caagatggcc accccatcga tgctgcccca atgggcatac atgcacatcg   18300
ccggacagga tgcttcggag tacctgagtc cgggtctggt gcagttcgcc cgcgccacag   18360
acacctactt caatctggga aataagttta gaaatcccac cgtagcgccg acccacgatg   18420
tgaccaccga ccgtagccag cggctcatgt tgcgcttcgt gcccgttgac cgggaggaca   18480
atacatactc ttacaaagtg cggtacaccc tggccgtggg cgacaacaga gtgctggata   18540
tggccagcac gttctttgac attaggggtg tgttggacag aggtcccagt ttcaaaccct   18600
attctggtac ggcttacaac tccctggctc ctaaaggcgc tccaaataca tctcagtgga   18660
ttgcagaagg tgtaaaaaat acaactggtg aggaacacgt aacagaagag gaaaccaata   18720
ctactactta cactttggc aatgctcctg taaaagctga agctgaaatt acaaaagaag    18780
gactcccagt aggtttggaa gtttcagatg aagaaagtaa accgatttat gctgataaaa   18840
catatcagcc agaacctcag ctgggagatg aaacttggac tgaccttgat ggaaaaaccg   18900
aaaagtatgg aggcagggct ctcaaacccg atactaagat gaaaccatgc tacgggtcct   18960 tgccaaacc tactaatgtg aaaggcgtc aggcaaaaca aaaacaacg gagcagccaa      19020 atcagaaagt cgaatatgat atcgacatgg agttttttga tgcggcatcg cagaaaacaa    19080
acttaagtcc taaaattgtc atgtatgcag aaaatgtaaa tttggaaact ccagacactc   19140
atgtagtgta caacctgga acagaagaca caagttccga agctaatttg ggacaacaat     19200
ctatgcccaa cagacccaac tacattggct tcagagataa ctttattgga cttatgtact   19260
ataacagtac tggtaacatg ggggtgctgg ctggtcaagc gtctcagtta aatgcagtgg   19320
ttgacttgca ggacagaaac acagaacttt cttaccaact cttgcttgac tctctgggcg   19380
acagaaccag atactttagc atgtggaatc aggctgtgga cagttatgat cctgatgtac   19440
```

```
gtgttattga aaatcatggt gtggaagatg aacttcccaa ctactgtttt ccactggacg   19500
gcataggtgt tccaacaacc agttacaaat caatagttcc aaatggagac aatgcgccta   19560
attggaagga acctgaagta aatggaacaa gtgagatcgg acagggtaat ttgtttgcca   19620
tggaaattaa ccttcaagcc aatctatggc gaagtttcct ttattccaat gtggctctat   19680
atctcccaga ctcgtacaaa tacaccccgt ccaatgtcac tcttccagaa aacaaaaaca   19740
cctacgacta catgaacggg cgggtggtgc cgccatctct agtagacacc tatgtgaaca   19800
ttggtgccag gtggtctctg gatgccatgg acaatgtcaa cccattcaac caccaccgta   19860
acgctggctt gcgttaccga tccatgcttc tgggtaacgg acgttatgtg cctttccaca   19920
tacaagtgcc tcaaaaattc ttcgctgtta aaaacctgct gcttctccca ggctcctaca   19980
cttatgagtg gaactttagg aaggatgtga acatggttct acagagttcc ctcggtaacg   20040
acctgcgggt agatggcgcc agcatcagtt tcacgagcat caacctctat gctactttt   20100 tccccatggc tcacaacacc gcttccaccc ttgaagccat gctgcggaat gacaccaatg   20160
atcagtcatt caacgactac ctatctgcag ctaacatgct ctaccccatt cctgccaatg   20220
caaccaatat tcccatttcc attccttctc gcaactgggc ggcttcaga ggctggtcat   20280 ttaccagact gaaaaccaaa gaaactccct ctttggggtc tggatttgac ccctactttg   20340
tctattctgg ttctattccc tacctggatg gtaccttcta cctgaaccac acttttaaga   20400
aggtttccat catgtttgac tcttcagtga gctggcctgg aaatgacagg ttactatctc   20460
ctaacgaatt tgaaataaag cgcactgtgg atggcgaagg ctacaacgta gcccaatgca   20520
acatgaccaa agactggttc ttggtacaga tgctcgccaa ctacaacatc ggctatcagg   20580
gcttctacat tccagaagga tacaaagatc gcatgtattc attttcaga aacttccagc   20640 ccatgagcag gcaggtggtt gatgaggtca attacaaaga cttcaaggcc gtcgccatac   20700
cctaccaaca caacaactct ggcttgtgg gttacatggc tccgaccatg cgccaaggtc   20760
aaccctatcc cgctaactat ccctatccac tcattggaac aactgccgta aatagtgtta   20820
cgcagaaaaa gttcttgtgt gacagaacca tgtggcgcat accgttctcg agcaacttca   20880
tgtctatggg ggcccttaca gacttgggac agaatatgct ctatgccaac tcagctcatg   20940
ctctggacat gaccttgag gtggatccca tggatgagcc caccctgctt tatcttctct   21000
tcgaagtttt cgacgtggtc agagtgcatc agccacaccg cggcatcatc gaggcagtct   21060
acctgcgtac accgttctcg gccggtaacg ctaccacgta agaagcttct tgcttcttgc   21120
aaatagcagc tgcaaccatg gcctgcggat cccaaaacgg ctccagcgag caagagctca   21180
gagccattgt ccaagacctg ggttgcggac cctatttttt gggaacctac gataagcgct   21240
tcccggggtt catggcccc gataagctcg cctgtgccat tgtaaatacg gccggacgtg   21300
agacgggggg agagcactgg ttggcttttcg gttggaaccc acgttctaac acctgctacc   21360
tttttgatcc ttttggattc tcggatgatc gtctcaaaca gatttaccag tttgaatatg   21420
agggtctcct gcgccgcagc gctcttgcta ccaaggaccg ctgtattacg ctggaaaaat   21480
ctacccagac cgtgcagggt ccccgttctg ccgcctgcgg acttttctgc tgcatgttcc   21540
ttcacgcctt tgtgcactgg cctgaccgtc ccatggacgg aaaccccacc atgaaattgc   21600
taactggagt gccaaacaac atgcttcatt ctcctaaagt ccagcccacc ctgtgtgaca   21660
atcaaaaagc actctaccat tttcttaata cccattcgcc ttattttcgc tcccatcgta   21720
cacacatcga aagggccact gcgttcgacc gtatggatgt tcaataatga ctcatgtaaa   21780
caacgtgttc aataaacatc actttatttt tttacatgta tcaaggctct gcattactta   21840
```

```
tttatttaca agtcgaatgg gttctgacga gaatcagaat gacccgcagg cagtgatacg   21900
ttgcggaact gatacttggg ttgccacttg aattcgggaa tcaccaactt gggaaccggt   21960
atatcgggca ggatgtcact ccacagcttt ctggtcagct gcaaagctcc aagcaggtca   22020
ggagccgaaa tcttgaaatc acaattagga ccagtgcttt gagcgcgaga gttgcggtac   22080
accggattgc agcactgaaa caccatcagc gacggatgtc tcacgcttgc cagcacggtg   22140
ggatctgcaa tcatgcccac atccagatct tcagcattgg caatgctgaa cggggtcatc   22200
ttgcaggtct gcctacccat ggcgggcacc caattaggct tgtggttgca atcgcagtgc   22260
agggggatca gtatcatctt ggcctgatcc tgtctgattc ctggatacac ggctctcatg   22320
aaagcatcat attgcttgaa agcctgctgg gctttactac cctcggtata aacatcccg    22380 caggacctgc tcgaaaactg gttagctgca cagccggcat cattcacaca gcagcgggcg   22440
tcattgttag ctatttgcac cacacttctg ccccagcggt tttgggtgat tttggttcgc   22500
tcgggattct cctttaaggc tcgttgtccg ttctcgctgg ccacatccat ctcgataatc   22560
tgctccttct gaatcataat attgccatgc aggcacttca gcttgccctc ataatcattg   22620
cagccatgag gccacaacgc acagcctgta cattcccaat tatggtgggc gatctgagaa   22680
aaagaatgta tcattccctg cagaaatctt cccatcatcg tgctcagtgt cttgtgacta   22740
gtgaaagtta actggatgcc tcggtgctcc tcgtttacgt actggtgaca gatgcgcttg   22800
tattgttcgt gttgctcagg cattagttta aagaggttc taagttcgtt atccagcctg    22860
tacttctcca tcagcagaca catcacttcc atgcctttct cccaagcaga caccaggggc   22920
aagctaatcg gattcttaac agtgcaggca gcagctcctt tagccagagg gtcatcttta   22980
gcgatcttct caatgcttct tttgccatcc ttctcaacga tgcgcacggg cgggtagctg   23040
aaacccactg ctacaagttg cgcctcttct ctttcttctt cgctgtcttg actgatgtct   23100
tgcatgggga tatgtttggt cttccttggc ttctttttgg ggggtatcgg aggaggagga   23160
ctgtcgctcc gttccggaga cagggaggat tgtgacgttt cgctcaccat taccaactga   23220
ctgtcggtag aagaacctga ccccacacgc gacaggtgt ttctcttcgg gggcagaggt    23280
ggaggcgatt gcgaagggct gcggtccgac ctggaaggcg gatgactggc agaacccctt   23340
ccgcgttcgg gggtgtgctc cctgtggcgg tcgcttaact gatttccttc gcggctggcc   23400
attgtgttct cctaggcaga gaaacaacag acatggaaac tcagccattg ctgtcaacat   23460
cgccacgagt gccatcacat ctcgtcctca gcgacgagga aaaggagcag agcttaagca   23520
ttccaccgcc cagtcctgcc accacctcta ccctagaaga taaggaggtc gacgcatctc   23580
atgacatgca gaataaaaaa gcgaaagagt ctgagacaga catcgagcaa gacccgggct   23640
atgtgacacc ggtggaacac gaggaagagt tgaaacgctt tctagagaga gaggatgaaa   23700
actgcccaaa acaacgagca gataactatc accaagatgc tggaaatagg gatcagaaca   23760
ccgactacct catagggctt gacggggaag acgcgctcct taaacatcta gcaagacagt   23820
cgctcatagt caaggatgca ttattggaca gaactgaagt gcccatcagt gtggaagagc   23880
tcagccgcgc ctacgagctt aacctctttt cacctcgtac tcccccaaa cgtcagccaa    23940 acggcacctg cgagccaaat cctcgcttaa acttttatcc agcttttgct gtgccagaag   24000
tactggctac ctatcacatc ttttttaaaa atcaaaaaat tccagtctcc tgccgcgcta   24060
atcgcacccg cgccgatgcc ctactcaatc tgggacctgg ttcacgctta cctgatatag   24120
cttccttgga agaggttcca aagatcttcg agggtctggg caataatgag actcgggccg   24180
caaatgctct gcaaaaggga gaaaatggca tggatgagca tcacagcgtt ctggtggaat   24240
```

```
tggaaggcga taatgccaga ctcgcagtac tcaagcgaag catcgaggtc acacacttcg   24300
catatcccgc tgtcaacctg cccectaaag tcatgacggc ggtcatggac cagttactca   24360
ttaagcgcgc aagtcccctt tcagaagaca tgcatgaccc agatgcctgt gatgagggta   24420
aaccagtggt cagtgatgag cagctaaccc gatggctggg caccgactct cccagggatt   24480
tggaagagcg tcgcaagctt atgatggccg tggtgctggt taccgtagaa ctagagtgtc   24540
tccgacgttt ctttaccgat tcagaaacct tgcgcaaact cgaagagaat ctgcactaca   24600
cttttagaca cggctttgtg cggcaggcat gcaagatatc taacgtggaa ctcaccaacc   24660
tggtttccta catgggtatt ctgcatgaga atcgcctagg acaaagcgtg ctgcacagca   24720
ccctgaaggg ggaagcccgc cgtgattaca tccgcgattg tgtctatctg tacctgtgcc   24780
acacgtggca aaccggcatg ggtgtatggc agcaatgttt agaagaacag aacttgaaag   24840
agcttgacaa gctcttacag aaatctctta aggttctgtg gacagggttc gacgagcgca   24900
ccgtcgcttc cgacctggca gacctcatct tcccagagcg tctcagggtt actttgcgaa   24960
acggattgcc tgactttatg agccagagca tgcttaacaa ttttcgctct ttcatcctgg   25020
aacgctccgg tatcctgccc gccacctgct gcgcactgcc ctccgacttt gtgcctctca   25080
cctaccgcga gtgcccccg ccgctatgga gtcactgcta cctgttccgt ctggccaact   25140
atctctccta ccactcggat gtgatcgagg atgtgagcgg agacggcttg ctggagtgtc   25200
actgccgctg caatctgtgc acgccccacc ggtccctagc ttgcaacccc cagttgatga   25260
gcgaaaccca gataataggc acctttgaat tgcaaggccc cagcagccaa ggcgatgggt   25320
cttctcctgg gcaaagttta aaactgaccc cgggactgtg gacctccgcc tacttgcgca   25380
agtttgctcc ggaagattac caccccctatg aaatcaagtt ctatgaggac caatcacagc   25440
ctccaaaggc cgaactttcg gcctgcgtca tcacccaggg ggcaattctg gcccaattgc   25500
aagccatcca aaaatcccgc caagaatttc tactgaaaaa gggtaagggg gtctaccttg   25560
acccccagac cggcgaggaa ctcaacacaa ggttccctca ggatgtccca acgacgagaa   25620
aacaagaagt tgaaggtgca gccgccgccc ccagaagata tggaggaaga ttgggacagt   25680
caggcagagg aggcggagga ggacagtctg gaggacagtc tggaggaaga cagtttggag   25740
gaggaaaacg aggaggcaga ggaggtggaa gaagtaaccg ccgacaaaca gttatcctcg   25800
gctgcggaga caagcaacag cgctaccatc tccgctccga gtcgaggaac ccggcggcgt   25860
cccagcagta gatgggacga gaccggacgc ttcccgaacc caaccagcgc ttccaagacc   25920
ggtaagaagg atcggcaggg atacaagtcc tggcgggggc ataagaatgc catcatctcc   25980
tgcttgcatg agtgcggggg caacatatcc ttcacgcggc gctacttgct attccaccat   26040
ggggtgaact ttccgcgcaa tgttttgcat tactaccgtc acctccacag cccctactat   26100
agccagcaaa tcccggcagt ctcgacagat aaagacagcg gcggcgacct ccaacagaaa   26160
accagcagcg gcagttagaa aatacacaac aagtgcagca acaggaggat taaagattac   26220
agccaacgag ccagcgcaaa cccgagagtt aagaaatcgg atctttccaa ccctgtatgc   26280
catcttccag cagagtcggg gtcaagagca ggaactgaaa ataaaaaacc gatctctgcg   26340
ttcgctcacc agaagttgtt tgtatcacaa gagcgaagat caacttcagc gcactctcga   26400
ggacgccgag gctctcttca acaagtactg cgcgctgact cttaaagagt aggcagcgac   26460
cgcgcttatt caaaaaggc gggaattaca tcatcctcga catgagtaaa gaaattccca   26520
cgccttacat gtggagttat caaccccaaa tgggattggc ggcaggcgcc tcccaggact   26580
actccacccg catgaattgg ctcagcgccg ggccttctat gatttctcga gttaatgata   26640
```

```
tacgcgccta ccgaaaccaa atacttttgg aacagtcagc tcttaccacc acgccccgcc   26700
aacaccttaa tcccagaaat tggcccgccg ccctagtgta ccaggaaagt cccgctccca   26760
ccactgtatt acttcctcga gacgcccagg ccgaagtcca aatgactaat gcaggtgcgc   26820
agttagctgg cggctccacc ctatgtcgtc acaggcctcg gcataatata aaacgcctga   26880
tgatcagagg ccgaggtatc cagctcaacg acgagtcggt gagctctccg cttggtctac   26940
gaccagacgg aatctttcag attgccggct gcgggagatc ttccttcacc cctcgtcagg   27000
ctgttctgac tttggaaagt tcgtcttcgc aaccccgctc gggcggaatc gggaccgttc   27060
aatttgtgga ggagtttact ccctctgtct acttcaaccc cttctccgga tctcctgggc   27120
attacccgga cgagttcata ccgaacttcg acgcgattag cgagtcagtg gacggctacg   27180
attgatgtct ggtgacgcgg ctgagctatc tcggctgcga catctagacc actgccgccg   27240
ctttcgctgc tttgcccggg aactcattga gttcatctac ttcgaactcc ccaaggatca   27300
ccctcaaggt ccgcccacg gagtgcggat ttctatcgaa ggcaaaatag actctcgcct    27360
gcaacgaatt ttctcccagc ggcccgtgct gatcgagcga gaccagggaa acaccacggt   27420
ttccatctac tgcatttgta atcaccccgg attgcatgaa agcctttgct gtcttatgtg   27480
tactgagttt aataaaaact gaattaagac tctcctacgg actgccgctt cttcaacccg   27540
gattttacaa ccagaagaac gaaacttttc ctgtcgtcca ggactctgtt aacttcacct   27600
ttcctactca caaactagaa gctcaacgac tacaccgctt ttccagaagc attttcccta   27660
ctaatactac tttcaaaacc ggaggtgagc tccaaggtct tcctacagaa acccttgggg   27720
tggaagcggg ccttgtagtg ctaggaattc ttgcgggtgg gcttgtgatt attctttgct   27780
acctatacac accttgcttc actttcttag tggtgttgtg gtattggttt aaaaaatggg   27840
gcccatacta gtcttgcttg ttttactttc gcttttggaa ccgggttctg ccaattacga   27900
tccatgtcta gacttcgacc cagaaaactg cacacttact tttgcacccg acacaagccg   27960
catctgtgga gttcatcgcc tctcttacga acttggcccc caacgacaaa aatttacctg   28020
catggtggga atcaaccccca tagttatcac ccagcaaagt ggagatacta agggttgcat   28080
tcactgctcc tgcgattcca tcgagtgcac ctacaccctg ctgaagaccc tatgcggcct   28140
aagagacctg ctaccaatga attaaaaaat gattaataaa aaatcactta cttgaaatca   28200
gcaataaggt ctctgttgaa atttttctccc agcagcacct cacttccctc ttcccaactc   28260
tggtattcta aaccccgttc agcggcatac tttctccata ctttaaaggg gatgtcaaat   28320
tttagctcct ctcctgtacc cacaatcttc atgtctttct tcccagatga ccaagagagt   28380
ccggctcagt gactccttca accctgtcta cccctatgaa gatgaaagca cctcccaaca   28440
cccctttata aacccagggt ttatttcccc aaatggcttc acacaaagcc caaacggagt   28500 tcttactttta aaatgtttaa ccccactaac aaccacaggc ggatctctac agctaaaagt   28560 gggagggggga cttacagtgg atgacaccaa cggttttttg aaagaaaaca taagtgccac   28620
cacaccactc gttaagactg gtcactctat aggtttacca ctaggagccg gattgggaac   28680
gaatgaaaat aaactttgta tcaaattagg acaaggactt acattcaatt caaacaacat   28740
ttgcattgat gacaatatta acaccttatg gacaggagtc aaccccaccg aagccaactg   28800
tcaaatcatg aactccagtg aatctaatga ttgcaaatta attctaacac tagttaaaac   28860
tggagcacta gtcactgcat ttgtttatgt tataggagta tctaacaatt ttaatatgct   28920
aactacacac agaaatataa attttactgc agagctgttt ttcgattcta ctggtaattt   28980
actaactaga ctctcatccc tcaaaactcc acttaatcat aaatcaggac aaaacatggc   29040
```

```
tactggtgcc attactaatg ctaaaggttt catgcccagc acgactgcct atcctttcaa  29100
tgataattct agagaaaaag aaaactacat ttacggaact tgttactaca cagctagtga  29160
tcgcactgct tttcccattg acatatctgt catgcttaac cgaagagcaa taaatgacga  29220
gacatcatat tgtattcgta taacttggtc ctggaacaca ggagatgccc cagaggtgca  29280
aacctctgct acaaccctag tcacctcccc atttaccttt tactacatca gagaagacga  29340
ctgacaaata aagtttaact tgtttatttg aaaatcaatt cacaaaatcc gagtagttat  29400
tttgcctccc ccttcccatt taacagaata caccaatctc tccccacgca cagctttaaa  29460
catttggata ccattagata tagacatggt tttagattcc acattccaaa cagtttcaga  29520
gcgagccaat ctggggtcag tgatagataa aaatccatcg ggatagtctt ttaaagcgct  29580
ttcacagtcc aactgctgcg gatgcgactc cggagtctgg atcacggtca tctgaaagaa  29640
gaacgatggg aatcataatc cgaaaacggt atcggacgat tgtgtctcat caaacccaca  29700
agcagccgct gtctgcgtcg ctccgtgcga ctgctgttta tgggatcagg gtccacagtg  29760
tcctgaagca tgattttaat agcccttaac atcaactttc tggtgcgatg cgcgcagcaa  29820
cgcattctga tttcactcaa atctttgcag taggtacaac acattattac aatattgttt  29880
aataaaccat aattaaaagc gctccagcca aaactcatat ctgatataat cgcccctgca  29940
tgaccatcat accaaagttt aatataaatt aaatgacgtt ccctcaaaaa cacactaccc  30000
acatacatga tctcttttgg catgtgcata ttaacaatct gtctgtacca tggacaacgt  30060
tggttaatca tgcaacccaa tataaccttc cggaaccaca ctgccaacac cgctccccca  30120
gccatgcatt gaagtgaacc ctgctgatta caatgacaat gaagaaccca attctctcga  30180
ccgtgaatca cttgagaatg aaaaatatct atagtggcac aacatagaca taatgcatg  30240 catcttctca taattttttaa ctcctcagga tttagaaaca tatcccaggg aataggaagc  30300
tcttgcagaa cagtaaagct ggcagaacaa ggaagaccac gaacacaact tacactatgc  30360
atagtcatag tatcacaatc tggcaacagc gggtggtctt cagtcataga agctcgggtt  30420
tcattttcct cacaacgtgg taactgggct ctggtgtaag ggtgatgtct ggcgcatgat  30480
gtcgagcgtg cgcgcaacct tgtcataatg gagttgcttc ctgacattct cgtattttgt  30540
atagcaaaac gcggccctgg cagaacacac tcttcttcgc cttctatcct gccgcttagc  30600
gtgttccgtg tgatagttca agtacaacca cactcttaag ttggtcaaaa gaatgctggc  30660
ttcagttgta atcaaaactc catcgcatct aatcgttctg aggaaatcat ccaagcaatg  30720
caactggatt gtgtttcaag caggagagga gagggaagag acggaagaac catgttaatt  30780
tttattccaa acgatctcgc agtacttcaa attgtagatc gcgcagatgg catctctcgc  30840
ccccactgtg ttggtgaaaa agcacagcta gatcaaaaga aatgcgattt tcaaggtgct  30900
caacggtggc ttccagcaaa gcctccacgc gcacatccaa gaacaaaaga ataccaaaag  30960
aaggagcatt ttctaactcc tcaatcatca tattacattc ctgcaccatt cccagataat  31020
tttcagcttt ccagccttga attattcgtg tcagttcttg tggtaaatcc aatccacaca  31080
ttacaaacag gtcccggagg gcgccctcca ccaccattct taaacacacc ctcataatga  31140
caaaatatct tgctcctgtg tcacctgtag cgaattgaga atggcaacat caattgacat  31200
gcccttggct ctaagttctt cttttaagttc tagttgtaaa aactctctca tattatcacc  31260
aaactgctta gccagaagcc ccccgggaac aagagcaggg gacgctacag tgcagtacaa  31320
gcgcagacct ccccaattgg ctccagcaaa aacaagattg gaataagcat attgggaacc  31380
gccagtaata tcatcgaagt tgctggaaat ataatcaggc agagtttctt gtaaaaattg  31440
```

```
aataaaagaa aaatttgcca aaaaaacatt caaaacctct gggatgcaaa tgcaataggt  31500
taccgcgctg cgctccaaca ttgttagttt tgaattagtc tgcaaaaata aaaaaaaaaa  31560
caagcgtcat atcatagtag cctgacgaac agatggataa atcagtcttt ccatcacaag  31620
acaagccaca gggtctccag ctcgaccctc gtaaaacctg tcatcatgat taaacaacag  31680
caccgaaagt tcctcgcggt gaccagcatg aataattctt gatgaagcat acaatccaga  31740
catgttagca tcagttaacg agaaaaaaca gccaacatag cctttgggta taattatgct  31800
taatcgtaag tatagcaaag ccacccctcg cggatacaaa gtaaaaggca caggagaata  31860
aaaaatataa ttatttctct gctgctgttc aggcaacgtc gcccccggtc cctctaaata  31920
cacatacaaa gcctcatcag ccatggctta ccagacaaag tacagcgggc acacaaagca  31980
caagctctaa agtgactctc caacctctcc acaatatata tatacacaag ccctaaactg  32040
acgtaatggg agtaaagtgt aaaaaatccc gccaaaccca acacacaccc cgaaactgcg  32100
tcaccaggga aaagtacagt ttcacttccg caatcccaac aggcgtaact tcctctttct  32160
cacggtacgt gatatcccac taacttgcaa cgtcattttc ccacggtcgc accgcccctt  32220
ttagccgtta accccacagc caatcaccac acgatccaca cttttttaaaa tcacctcatt  32280 tacatattgg caccattcca tctataaggt atattatata gatag                 32325
```

GENERATION OF REPLICATION COMPETENT VIRUSES FOR THERAPEUTIC USE

This application is a division of Ser. No. 11/288,821 filed Nov. 28, 2005, which claims the benefit of Ser. No. 60/632,671 filed Dec. 1, 2004. Each of these applications is hereby incorporated herein its its entirety by reference.

This application incorporates by reference a 45.9 kb text file created on Jun. 22, 2009 and named "BSP53924_sequencelisting.txt," which is the sequence listing for this application.

FIELD OF THE INVENTION

The present invention relates to the generation of replication competent viruses having therapeutic applications.

BACKGROUND OF THE INVENTION

The goal of gene therapy is to deliver genetic material of therapeutic value to a target tissue in a safe and efficient manner. Safety is often related to how much damage is done to the normal tissues of the patient during treatment. Efficiency can be looked at as a ratio of desired result, e.g. reduction of tumor load, to acceptable dosage level, where the parameters which contribute to making a dosage level "acceptable" can include issues of injection volume, frequency, etc. Therefore, any improvements that result in an increase in the selectivity and efficiency of gene therapy are clearly desirable.

Viral vectors derived from adenoviruses, have been the most studied delivery agents for this type of therapy (Jolly, D. (1994) Cancer Gene *Therapy* 1:51-64). Replication-defective vectors are limited in their usefulness due to their ability to only kill tumor cells that have been directly infected with virus. Viral vectors developed from oncolytic (i.e. replication-competent) viruses are more attractive choices for cancer therapeutics because they not only selectively target tumor cells, but they can, through replication within the infected tumor cells, amplify and spread the input dose of infective virus throughout the tumor cell mass.

The potential use of vectors derived from oncolytic viruses, such as adenovirus, in gene therapy can be further increased by "arming" the viruses with therapeutic transgenes, i.e. engineering them to contain therapeutic proteins or other molecules whose in vivo expression can impact tumor survival (Hermiston, T. (2000) *J. Clin. Inv.* 105:1169-1172). The combination of viral replication within tumor cells and the activity of the therapeutic molecule expressed within the cells can provide a synergistic assault on a tumor.

The incorporation of therapeutic transgenes into an oncolytic virus is a complex process. The insertion event needs to occur in a site that maintains the replication competence of the viral agent, which is complicated as viruses maximize their coding capacity by generating highly complex transcription units controlled by multiple promoters and alternative splicing (Akusjarui and Stevenin (2003 *Curr. Top. Microbiol. Immunol.* 272:253-286). Consequently, the choice of insertion sites for therapeutic genes has been limited primarily to regions known to be non-essential for viral DNA replication in vitro (Hawkins et al. (2001) *Gene Ther.* 8:1123-1131; Kurihara et al. (2002) *J. Clin. Invest.* 106:763-771) or by the replacement of a deleted region of the viral genome to create the oncolytic virus (Freytag et al. (1998) *Human Gene Ther.* 9:1323-1333; Lee et al. (2001) *Cancer Gene Ther.* 8:397-404). While these approaches allow for therapeutic gene insertion and expression, they are dependent upon a high level of understanding of the viral biology (i.e. sites non-essential for viral replication), a known viral genome sequence (for use in genetic engineering or utilization of endogenous restriction enzyme sites) and the presence of molecular biology systems for genomic manipulations that may not be currently available for non-Ad5-based systems.

In view of the above, there is a need for a method for generating replication competent viruses which contain genetic elements, e.g., a gene which encodes a therapeutic protein or RNA, positioned within the viral genome such that expression of the genetic element occurs. Of particular utility would be a method that identifies functional insertion sites within replication competent viruses whose genomic structure has not yet been elucidated.

SUMMARY OF THE INVENTION

The present invention provides a novel method for identifying functional insertion sites within the genome of a replication competent virus and for generating replication competent viruses which comprise a genetic element of interest or an expression cassette inserted in one of the identified insertion sites.

In particular, the method of the present invention comprises the steps of
(a) mixing the genomic DNA of a replication competent target virus with a donor DNA comprising a transposon under conditions that allow transposition, wherein said transposon comprises at least one genetic element of interest and inserts into said target viral genome in a non-biased manner; and
(b) isolating replication competent product viruses from said step (a) which express said genetic element of interest.

In one embodiment of the present invention, the replication competent target virus is an animal virus, preferably an oncolytic animal virus. In a preferred embodiment, the animal virus is an adenovirus, VSV, NDV, HSV or vaccinia virus. Particularly preferred are adenoviruses belonging to groups B and C. A particularly preferred Group C adenovirus is Ad5.

In one embodiment of the present invention, the genomic DNA of the replication competent target virus is present within a plasmid. In a preferred embodiment, the genomic DNA of the replication competent target virus within the plasmid is flanked by restriction enzyme sites. Particularly preferred is an embodiment in which the restriction enzyme sites flanking the genomic DNA of the replication competent target virus within the plasmid are identical.

In one embodiment of the invention, the donor DNA comprising the transposon is a plasmid and further comprises an origin of replication. A preferred origin of replication is the R6K origin of replication.

In one embodiment of the present invention, the transposon comprises a genetic element of interest that is a gene that encodes a reporter protein, where the reporter protein includes, but is not limited to, green fluorescing protein (GFP), LacZ, renilla luciferase or firefly luciferase. Particularly preferred is a gene encoding GFP.

In another embodiment of the present invention, the genetic element of interest is a gene that encodes a therapeutic protein, where the therapeutic protein can be, but is not limited to, an immunomodulatory protein, an antibody, a symporter, a pro-drug converting enzyme, a fusogenic glycoprotein, or fragments thereof. Preferred immunomodulatory proteins include molecules identified as cytokines or chemokines.

In another embodiment of the present invention, the genetic element of interest encodes a therapeutically useful RNA molecule including, but not limited to, shRNA or antisense RNA.

In one embodiment of the present invention, the transposon further comprises an expression element located upstream from, and operably linked to, the genetic element of interest, such that the expression element and the genetic element of interest comprise an "expression cassette". In a preferred embodiment, the expression element is a eukaryotic promoter. Preferred promoters include, but are not limited to, traditional Pol II promoters (e.g. E2F or hTERT), Pol III promoters (e.g. U6 or H1) or viral promoters (e.g. CMV, SV40, HSV TK or Ad MLP). A particularly preferred promoter is the early SV40 promoter.

In another embodiment of the present invention, the expression element is a eukaryotic splice acceptor sequence. Particularly preferred splice acceptor sequences include SEQ ID NO: 1, SEQ ID NO: 2 or SEQ ID NO: 3. Particularly preferred is the splice acceptor sequence of SEQ ID NO: 1.

In another embodiment of the present invention, the transposon further comprises restriction enzyme sites unique to the transposon, i.e. not present in the genomic DNA of the replication competent target virus, which are located close to the ends of the transposon. In a preferred embodiment, the restriction enzyme sites are identical. A particularly preferred restriction enzyme site is a PmeI site.

In one embodiment of the present invention, the transposon is one that employs an ATP-dependent utilizing regulatory protein in the transposition process. Particularly preferred is a Tn-7 based transposon.

In another embodiment of the present invention, the transposon further comprises a selectable/identifiable gene, such as a gene that confers drug resistance or one that provides a mechanism for visual identification of cells. Preferred genes that confer drug resistance include genes that confer antibiotic resistance. Particularly preferred is a gene that confers chloramphenicol resistance. Among the genes that allow for visual identification of cells are those encoding GFP, renilla luciferase, or firefly luciferase.

The present invention also provides for replication competent viruses made by the methods described herein and for the use of these viruses as vectors for the delivery of therapeutic molecules during gene therapy.

BRIEF DESCRIPTION OF THE FIGURES

The foregoing and other objects of the present invention, the various features thereof, as well as the invention itself may be more fully understood from the following description, when read together with the accompanying drawings.

Figure 3:
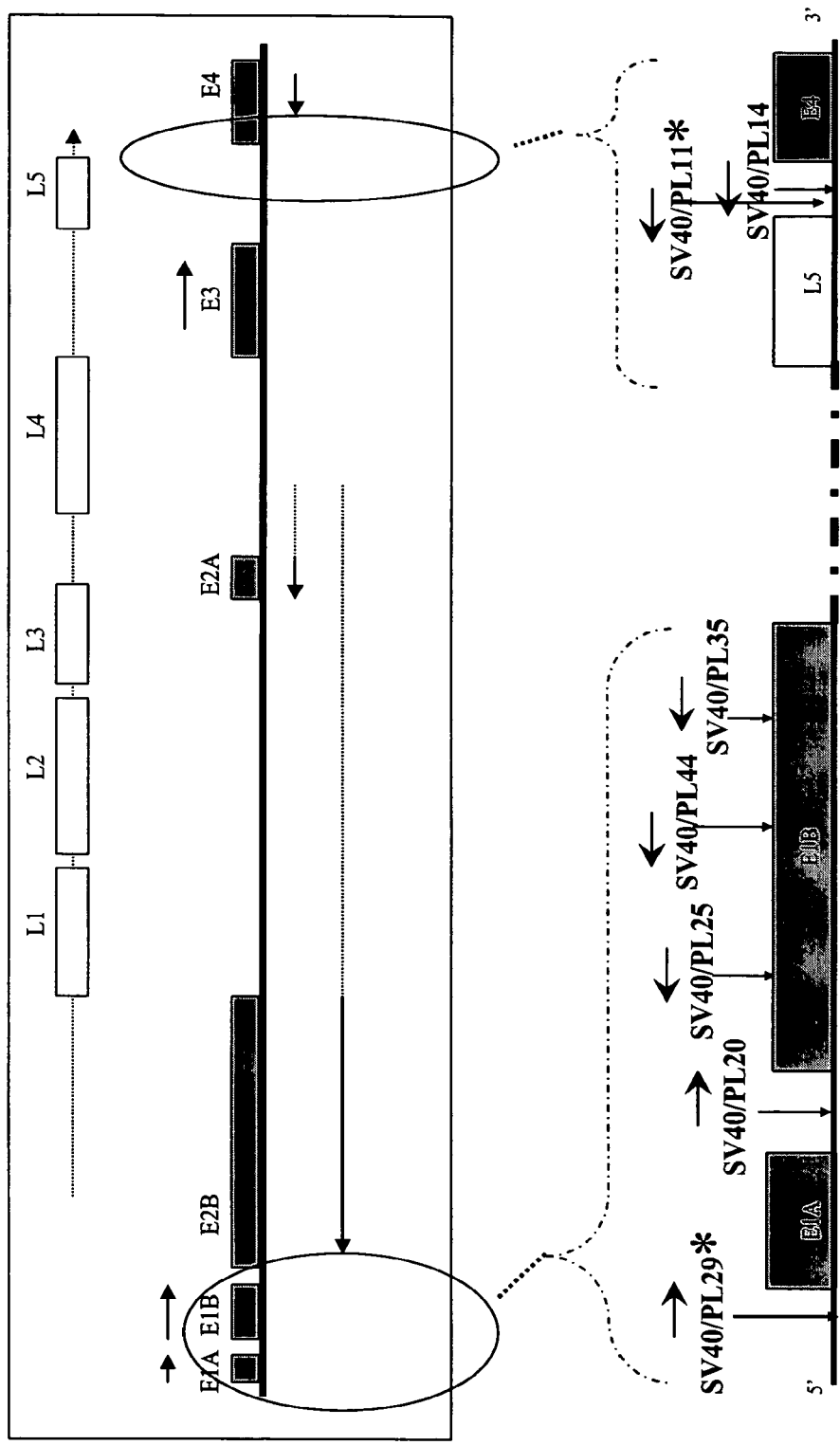
FIG. 3. Insertion sites of SV40/GFP containing transposons within the Ad 5 genome The outlined area illustrates the transcription and translation map of Ad5. The early mRNAs are designated E. Late mRNAs are designated L. Black ovals circle the designated "E1" and "L5 to E4" regions in the translation map of Ad5 and are enlarged in the map below, which indicates the site of insertion (vertical arrow) of a transposon comprising an SV40/GFP expression cassette within the Ad5 genome in each of a number of product viruses (see Example 4). Horizontal arrows above each product virus name indicate the transcriptional direction of SV40/GFP expression in that virus. The open dotted line represents the remaining Ad5 genome between E1 B and L5.

Panel A: the original virus, AdCJ51 (○); and two product viruses, Ad5/PL11/SV40/GFP (□) and Ad5/PL29/SV40/GFP(Δ), in which the SV40/GFP expression cassette had been determined to have been inserted in opposite orientations within the viral genome (see FIG. 3);

Panel B: Ad5/PL11/SV40/GFP (□); and Ad5/PL11/TK/RL (○); Ad5/PL11/CMV/Luc (◆) and Ad5/PL11/CMV/LacZ (▲), where the expression cassette replacements have the same orientation within the Ad 5 genome as the original SV40/GFP expression cassette; and Panel C: Ad5/PL29/SV40/GFP (Δ→); Ad5/PL29/CMV/Luc (◊→, ●←)); Ad5/PL29/TK/RL (■→, ▲←)) and Ad5/

PL29/CMV/LacZ (☐→), where the expression cassette replacements are oriented in both directions, as indicated by the arrows.

Figure 5:
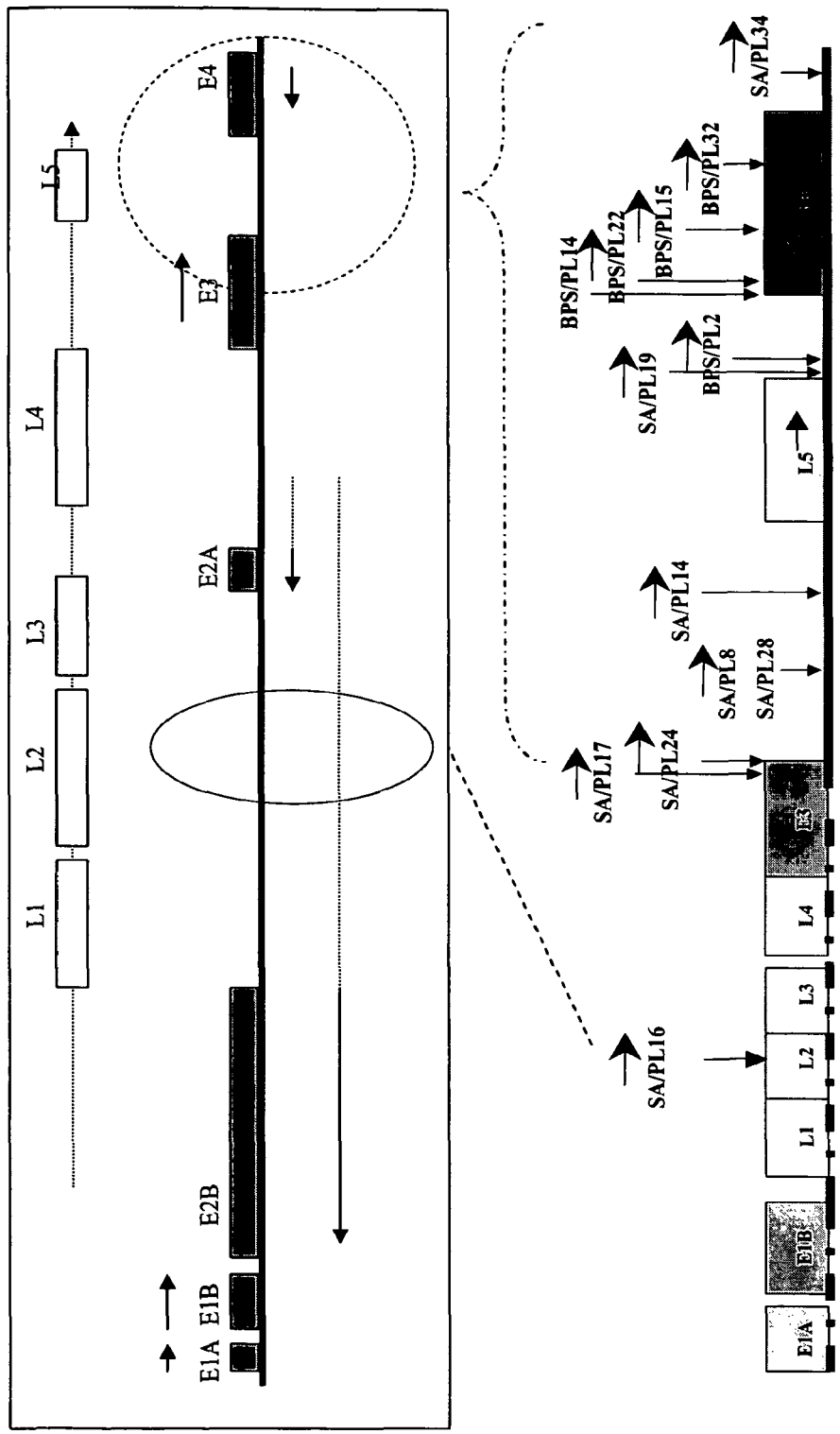

FIG. 5. Insertion Sites of Splice Acceptor/GFP transposons within the Ad5 genome The outlined area illustrates the transcription and translation map of Ad5. The early mRNAs are designated E. Late mRNAs are designated L. Black ovals circle the designated "E1" and "L5 to E4" regions of the transcription/translation map of Ad5 and are enlarged in the map below, which indicates the site of insertion (vertical arrow) of these transposons. Horizontal arrows above the product virus name indicate the transcriptional direction of the GFP expression in that viral construct.

Figure 6A:
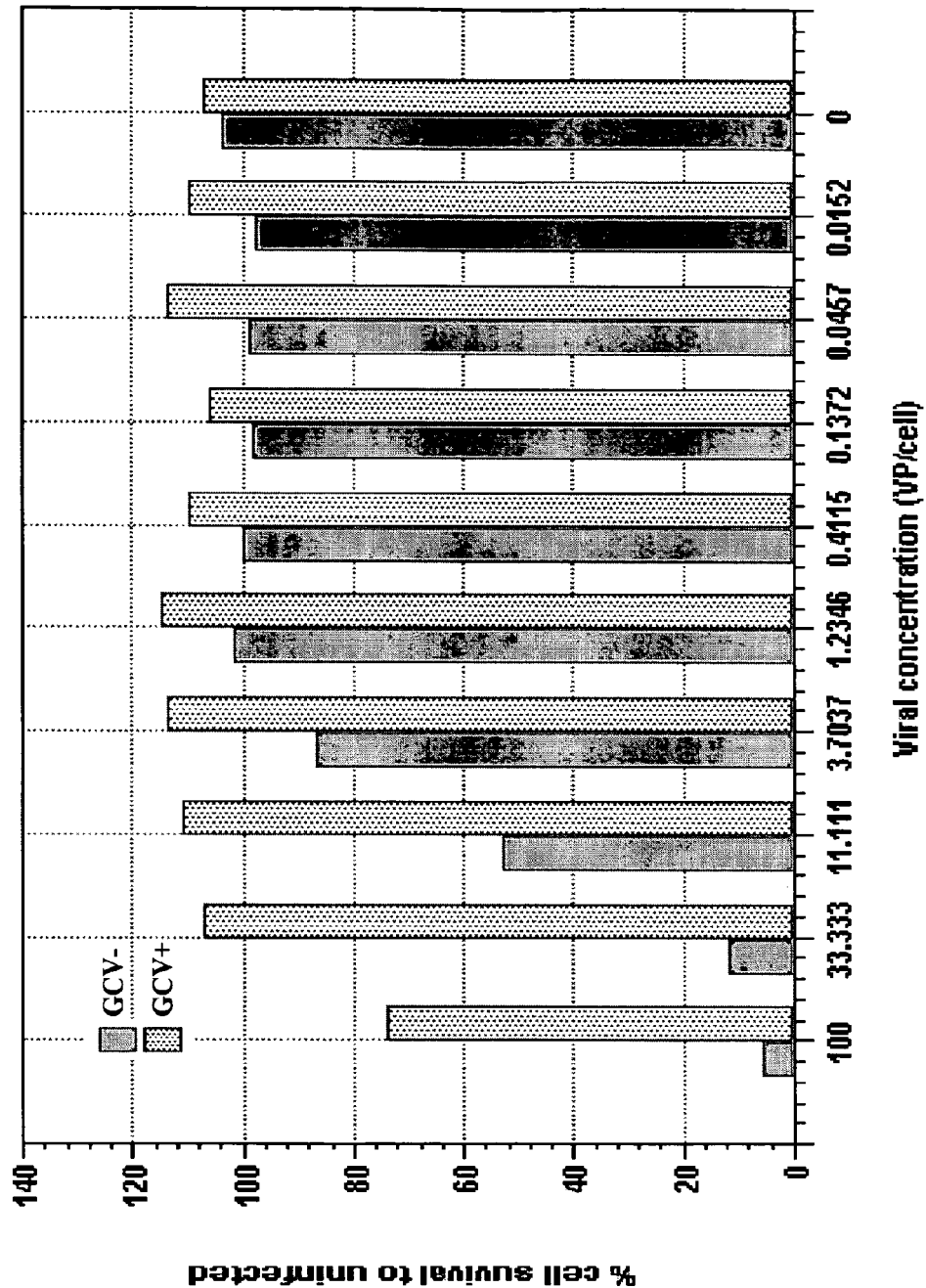
Figure 6B:
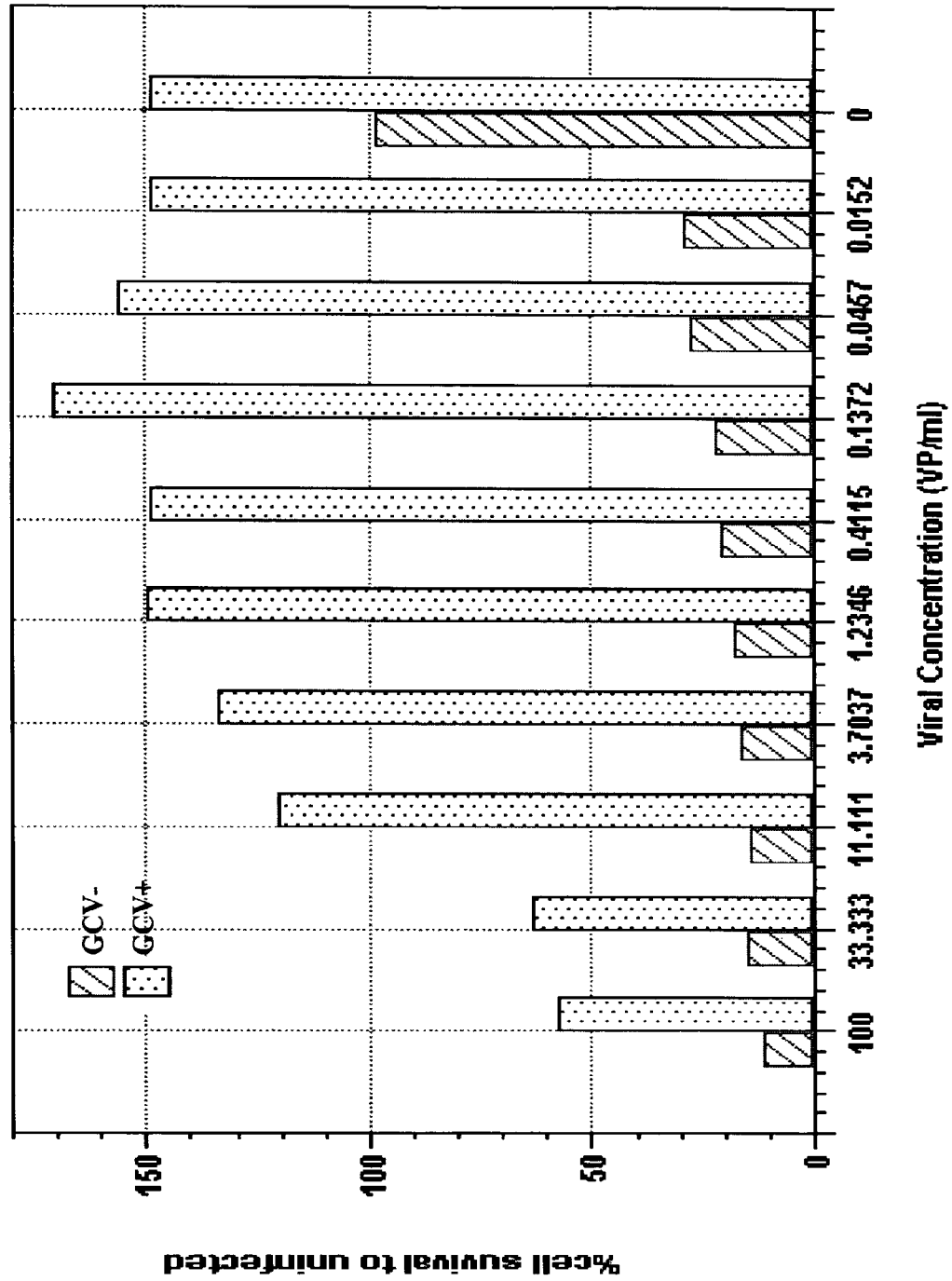

FIG. 6: Cytotoxicity of ColoAd1/PL30/TK/TK adenovirus with and without ganciclovir (GCV). MTS assays to measure potency were performed using the ColoAd1/PL30/TK/TK virus, which was derived from the ColoAd1 virus (SEQ ID NO: 22) as described in Example 9 and contains an expression cassette comprising a thymidine kinase gene, operably linked to a thymidine kinase promoter. Potency of this viral construct was examined in both a normal cell line (HUVEC; FIG. 6A) and in a lung cancer cell line (A549; FIG. 6B). Cytotoxicity in each cell line was determined with and without the addition of 20 uM ganciclovir, 24 hrs post infection (see Example 9).

DETAILED DESCRIPTION OF THE INVENTION

All publications, including patents and patent applications, mentioned in this specification are herein incorporated by reference to the same extent as if each individual publication was specifically and individually indicated to be incorporated by reference in its entirety.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Standard reference works setting forth the general principles of recombinant DNA technology include Sambrook, J., et al. (1989) *Molecular Cloning,: A Laboratory Manual,* 2d Ed., Cold Spring Harbor Laboratory Press, Planview, N.Y.; McPherson, M. J., Ed. (1991) *Directed Mutagenesis: A Practical Approach*, IRL Press, Oxford; Jones, J. (1992) *Amino Acid and Peptide Synthesis*, Oxford Science Publications, Oxford; Austen, B. M. and Westwood, O. M. R. (1991) *Protein Targeting and Secretion*, IRL Press, Oxford. Any suitable materials and/or methods known to those of ordinary skill in the art can be utilized in carrying out the present invention; however, preferred materials and/or methods are described. Materials, reagents and the like to which reference is made in the following description and examples are obtainable from commercial sources, unless otherwise noted.

DEFINITIONS

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

As used herein, the term "replication competent virus" refers to a virus which contains all the information within it's genome to allow it to replicate within a cell: i.e. it either produces the protein or induces the necessary host proteins.

As used herein, the term "target virus" refers to a replication competent virus capable of undergoing transposition, as contemplated by the invention. While the target virus will usually be a virus which has not previously undergone transposition, it is possible to use as a target virus a replication competent virus which has already undergone a round of transposition.

As used herein, the term "product virus" refers to the replication competent virus produced when a "target virus" has undergone transposition by the method of the invention.

As used herein, a "functional insertion site" within a replication competent virus refers to a site within that virus where, when a genetic element, operably linked to an expression element (i.e. a eukaryotic promoter or eukaryotic splice acceptor sequence) is inserted into that site, expression can occur.

As used herein, the term "genetic element of interest" refers to a nucleic acid sequence that is introduced into a transposon and that encodes a protein or RNA molecule whose expression is useful in the present invention.

A genetic element of interest includes genes that encode reporter proteins, i.e. proteins that are easily assayed or identified, e.g. green fluorescent protein (GFP), renilla luciferase, or firefly luciferase. A genetic element of interest, as used herein, also encompasses any gene encoding a protein, protein fragment or peptide (or modifications thereof) for which a therapeutic purpose can be envisioned. Examples include, but are not limited to, genes encoding immunomodulatory proteins, antibodies, symporter, fusogenic glycoproteins or pro-drug converting enzymes.

The term "genetic element of interest" also includes genes encoding RNA molecules, such as antisense RNA or shRNA, whose in vivo expression can result in modulation of cellular properties (e.g. cell growth, chemotherapeutic sensitization) by altering the expression levels of a targeted cellular protein (Karkare et al. *Appl. Biochem. Biotechnol.* (2004) 119:1-12).

As used herein, "useful" means that a protein or RNA expressed from a product virus would be useful in the evaluation or identification of the replication competent product viruses of the invention (e.g. the product of a reporter gene) or useful in therapeutic applications (e.g. the product of a gene encoding a therapeutic protein or an RNA).

As used herein, a "therapeutic protein" refers to a protein, protein fragment, or peptide that would be expected to provide some therapeutic benefit to an organism when expressed in vivo.

As used herein, the term "expression element" refers to a nucleic acid sequence located upstream from, and operably linked to, a genetic element of interest, and that facilitates expression of the genetic element of interest within the product virus. The expression element can be a promoter, e.g. a traditional POL II promoter; e.g. E2F or hTERT (Wu et al. *Trends in Mol. Med.* (2003) 9:421-429, a POL III promoter (e.g. U6) or a viral promoter (e.g. SV40, CMV, TK or MLP). Alternatively, an expression element can be a eukaryotic splice acceptor sequence, e.g. SEQ ID NO: 1, SEQ ID NO: 2, or SEQ ID NO: 3.

As used herein, the term "expression cassette" refers to a nucleic acid sequence that contains both a genetic element of interest and an expression element upstream from, and operably linked to, the genetic element, so that when the expression cassette is inserted in the proper orientation within the viral genome, the protein or RNA encoded by the genetic element is expressed. As used herein, an expression cassette comprising an SV40 promoter and a GFP reporter gene is represented as "SV40/GFP".

As used herein, the term "genomic DNA of the replication competent target virus" refers to the viral genomic DNA into which a transposon is inserted by the method of the invention.

As used herein, the term "product virus" refers to a genomic DNA of the replication competent target virus of the invention which has had a transposon inserted into it by the method of the invention.

As used herein, the term "non-biased" refers to the insertion of a transposon within a viral genome where the choice of insertion site is not substantially influenced by or dependent on particular sequences within the viral genome and is, therefore, considered random.

As used herein, the term "optimally expresses" or "optimal expression" refers to the characterization of a product virus comprising a genetic element of interest, when compared to the other isolated product viruses comprising that genetic element. The most straightforward comparative measurement of expression of a genetic element from a product virus would be measurement of the level of expression of the gene product encoded by that genetic element, i.e. that product virus demonstrating the highest level of expression of the protein encoded by the genetic element of interest would be ranked as that showing "optimal expression". However, also contemplated within the scope of the invention is measurement of "optimal expression" of a gene product by a product virus under varying conditions such as level of tissue-specific gene expression, expression in certain microenvironments (e.g. hypoxic, glucose deprived) or other measurements which would be indicative of relative in vitro or in vivo potency, etc.

As used herein, the term "adenovirus", refers to any of the 50+ human adenoviral serotypes currently known, or isolated in the future. See, for example, Strauss, "Adenovirus infections in humans," in The Adenoviruses, Ginsberg, ed., Plenum Press, New York, N.Y., pp. 451-596 (1984). These serotypes are classified in the subgroups A-F (see, Shenk, "Adenoviridae: The Viruses and Their Replication," in Fields Virology, Vol. 2, Fourth Edition, Knipe, ea., Lippincott Williams & Wilkins, pp. 2265-2267 (2001)

As used herein, the term "potency" refers to the lytic potential of a virus and represents its ability to replicate, lyse, and spread. For the purposes of the instant invention, potency is a value which compares the cytolytic activity of a given product virus of the invention to that of Ad5 in the same cell line, i.e. potency=$IC_{50}$ of X/$IC_{50}$ of Ad5, where X is the particular product virus being examined and wherein the potency of Ad5 is given a value of 1.

As used herein, the term "oncolytic virus" refers to a virus that preferentially kills cancer cells as compared with normal cells.

As used herein, the term "therapeutic index" or "therapeutic window" refers to a number indicating the oncolytic potential of a given virus and is determined by dividing the potency of the virus in a cancer cell line by the potency of the same virus in a normal (i.e. non-cancerous) cell line.

As used herein, the term "modified" refers to a molecule with a nucleotide or amino acid sequence differing from a naturally-occurring, e.g. a wild-type nucleotide or amino acid sequence. A modified molecule retains the function or activity of a wild-type molecule; i.e. a modified product virus may retain its oncolytic activity or therapeutic benefit. Modifications include mutations to nucleic acids as described below.

As used herein, "mutation" with reference to a polynucleotide or polypeptide, refers to a naturally-occurring, synthetic, recombinant, or chemical change or difference to the primary, secondary, or tertiary structure of a polynucleotide or polypeptide, as compared to a reference polynucleotide or polypeptide, respectively (e.g., as compared to a wild-type polynucleotide or polypeptide). Mutations include such changes as, for example, deletions, insertions, or substitutions. Polynucleotides and polypeptides having such mutations can be isolated or generated using methods well known in the art.

As used herein, the term "therapeutically effective dose" or "effective amount" refers to that amount of product virus that ameliorates the symptoms or conditions of a disease. A dose is considered a therapeutically effective dose in the treatment of cancer or its metastasis when tumor or metastatic growth is slowed or stopped, or the tumor or metastasis is found to shrink in size, so as to lead to an extension in life-span for the subject. For other disease states, appropriate endpoints for defining a therapeutically effective dose would be within the knowledge of one skilled in the art.

Generation of Viruses of the Invention

The present invention provides a novel method for identifying functional insertion sites within the genome of a replication competent target virus and for generating replication competent viruses ("product viruses") which comprise a genetic element of interest or an expression cassette inserted in one of the identified insertion sites. The product viruses of the invention can express the inserted genetic element following infection of cells in vitro and in vivo.

The method for identifying functional insertion sites within the replication competent viruses of the invention comprises mixing the genomic DNA of a replication competent target virus with a donor DNA under conditions that allow formation of replication competent product viruses comprising said transposon, where the donor DNA comprises a transposon capable of inserting into the genome of the target virus in a non-biased manner, and where the transposon comprises a genetic element of interest or an expression cassette.

The replication competent product viruses can be evaluated to determine their utility, using assays that directly measure protein expression or that measure an activity of the inserted genetic element. A comparison of such values within a group of isolated replication competent viruses, containing insertions at different positions within the viral genome, allows selection of the particular product virus best suited for a given therapeutic situation.

Genomic DNA of the Replication Competent Target Virus.

The genomic DNA of the replication competent target virus of the present invention can be that of any desired virus, preferably an animal virus (i.e. a virus that can replicate in an animal or an animal cell) and is most preferably an oncolytic animal virus including, but not limited to, adenovirus, VSV, HSV or vaccinia virus. An important advantage of the present invention is that it allows one to use the genomic DNA of a virus for which specific prior knowledge regarding viral genomic organization or sequence is not available. A preferred genomic viral DNA for use in the present invention is that of an adenovirus, and particularly preferred is an adenovirus from Groups B or C. A particularly preferred adenovirus within Group C is Ad5.

Wild-type viruses, as well as viral derivatives containing deletions of non-essential polynucleotides within the viral genome, e.g. the E3 region in adenovirus (Berkner and Sharp (1983) *Nucleic Acid Res.* 11:6003-6020) are contemplated to be useful in the present invention. Use of replication competent viruses which have a reduced viral genome, is preferred, as the total amount of DNA which can be packaged into a virus is limited by size constraints (for example, see Bett et al.

(1993) *J. Virol.* 10:5911-5921). Therefore, use of a smaller starting viral genome (either naturally occurring or artificially made) allows insertion of transposons that contain larger genetic elements of interest or expression cassettes and also allows for the possible insertion of more than one transposon within the genomic DNA of the replication competent target virus. Also useful are viral derivatives which have been identified as having an increased potency toward particular cell types, such as ColoAd1 (SEQ ID NO: 22), which has been shown to have increased potency toward colon tumor cells.

Genomic DNA of the replication competent target viruses useful in the present invention can be in a linear form or it can be present in a plasmid and be linearized when desired, i.e. to allow more efficient transfection to occur (Berkner and Sharp (1983) *Nucleic Acid Res.* 11:6003-6020). In a preferred embodiment, the genomic DNA of the replication competent target virus is present in a plasmid, which facilitates initial selection and amplification of product viruses. Where the genomic DNA of the replication competent target virus is present in a plasmid, the viral DNA should be easily excisable from the plasmid. In one embodiment, restriction enzyme sites flank the viral DNA within the plasmid. In a preferred embodiment, the restriction enzyme sites are identical. In a particularly preferred embodiment, the genomic DNA of the replication competent target virus is flanked by PacI sites (see FIG. 1). PacI, however, is only one choice of restriction enzyme site and determination of other useful restriction enzyme sites is well within the knowledge of one skilled in the art.

Donor DNA

The donor DNA of the present invention, which comprises a transposon, can be in a linear form, such as a phage, or can be a plasmid.

A transposon useful in the present invention has the ability to insert itself into a viral genome in a non-biased manner, i.e. the choice of insertion site is not influenced by or dependent on particular sequences within the viral genome. Transposons that use ATP-utilizing regulatory proteins are contemplated for use in the invention, provided that appropriate mutations in the ATP-utilizing protein have been made such that insertion is non-biased (see U.S. Ser. No. 10/024,809). Examples of such transposons are Tn5090/Tn420 and Tn7. Particularly preferred is a Tn7-based transposon (Biery et al. (2000) *Nucleic Acid Res.* 28:1067-1077).

A transposon useful in the present invention comprises a genetic element of interest.

In one embodiment, the genetic element of interest is a gene, often referred to as a "reporter gene", that encodes a detectable gene product, i.e. a product whose expression can be easily assayed or identified. For instance, the reporter gene may encode a gene product that, by enzymatic activity, gives rise to a detection signal based on color, fluorescence, or luminescence. Many reporter genes are known to those of skill in the art and others may be identified or synthesized by methods known to those of skill in the art. Useful reporter genes include, but are not limited to, green fluorescing protein (GFP), LacZ, renilla luciferase or firefly luciferase. A particularly preferred reporter gene is GFP. Assays for measuring these proteins are well known in the art.

In another embodiment of the present invention, the genetic element of interest is a gene that encodes a therapeutic protein. A therapeutic protein, as used herein, refers to a protein, protein fragment or peptide, or a modification thereof, that would be expected to provide some therapeutic benefit to an organism when expressed in vivo. Therapeutic proteins contemplated in the present invention include, but are not limited to, proteins which are immunomodulatory proteins, antibodies, symporters, fusogenic glycoproteins or pro-drug converting enzymes, and encompass any protein, protein fragment or polypeptide whose expression within a cell would be expected, by one of skill in the art, to provide a therapeutic benefit (e.g. a cytotoxic effect, growth inhibitory effect etc.).

In one embodiment, the therapeutic protein of the present invention can be a pro-drug activator, such as cytosine deaminase (see, U.S. Pat. Nos. 5,631,236; 5,358,866; and 5,677,178). In another embodiment, the therapeutic protein can be a known inducer of cell-death, e.g. apoptin or adenoviral death protein, or a fusion protein, e.g. fusogenic membrane glycoprotein (Danen-Van Oorschot et al. (1997) *Proc. Nat. Acad. Sci.* 94:5843-5847; Tollefson et al. (1996) *J. Virol.* 70:2296-2306; Fu et al. (2003) *Mol. Therapy.* 7: 48-754, 2003; Ahmed et al. (2003) *Gene Therapy* 10:1663-1671; Galanis et al. (2001) *Human Gene Therapy* 12(7): 811-821).

Alternatively, a therapeutic protein of the invention can be a member of a symporter family (e.g. sodium/iodide symporter, NIS) that would enable a therapeutic molecule to be more effectively targeted to the tumor cell.

Other therapeutic proteins, or fragments thereof, useful in the present invention, include those that encode immunomodulatory proteins, such as cytokines or chemokines. Examples include interleukin 2, U.S. Pat. No. 4,738,927 or 5,641,665; interleukin 7, U.S. Pat. No. 4,965,195 or 5,328,988; and interleukin 12, U.S. Pat. No. 5,457,038; tumor necrosis factor alpha, U.S. Pat. No. 4,677,063 or 5,773,582; interferon gamma, U.S. Pat. No. 4,727,138 or 4,762,791; or GM CSF, U.S. Pat. No. 5,393,870 or 5,391,485, Mackensen et al. (1997) *Cytokine Growth Factor Rev.* 8:119-128). Additional immunomodulatory proteins include macrophage inflammatory proteins, including MCP-3. Monocyte chemotactic protein (MIP-3 alpha) may also be used.

In another embodiment, the genetic element of interest encodes a protein whose expression is known to enhance the ability of an oncolytic virus to eradicate the tumor, although not having any direct impact on the tumor itself. These genes include encoding proteins that (1) compromise MHC class I presentation (Hewitt et al. (2003) *Immunology* 110: 163-169), (2) block complement activity, (3) inhibit IFNs and IFN-induced mechanisms, (4) enhance NK cell based killing (Orange et al., (2002) *Nature Immunol.* 3: 1006-1012; Mireille et al. (2002) *Immunogenetics* 54: 527-542; Alcami (2003) *Nature Rev. Immunol.* 3: 36-50; (5) down regulate the immune response (e.g. IL-10, TGF-Beta, Khong and Restifo (2002) *Nature Immunol.* 3: 999-1005; 2002) and (6) act to breakdown the extracellular matrix and enhance spread of the virus within the tumor (e.g. metalloproteinases) (Bosman and Stamenkovic (2003) *J. Pathol.* 2000: 423-428; Visse and Nagase (2003) *Circulation Res.* 92: 827-839).

In another embodiment of the invention, the genetic element of interest encodes a protein that can provide a safety mechanism, such that expression of the protein can be used to abort viral infection when necessary, e.g. the Herpes Simples Virus (HSV) thymidine kinase, which, when expressed in the presence of ganciclovir (GCV), converts GCV into a triphosphate which is toxic to both cellular and viral replication (see Example 9; FIGS. 6A and B).

In a different embodiment, the genetic element of interest comprising the transposon encodes a therapeutically useful RNA molecule, i.e. shRNA (Dorsett and Tuschl (2004) *Nature Rev. Drug Disc.* 3:318-329) or antisense RNA, which hybridizes to a coding mRNA nucleic acid sequence, e.g., a cancer protein sequence. Expression of these types of molecules within a tumor cell can provide a therapeutic benefit by reducing the translation and/or stability of the targeted mRNA. In mammalian cells, short, e.g., 21 nucleotide, double stranded small interfering RNAs (shRNA) have been shown to be effective at inducing an RNAi response (Elbashir, et al. (2001) *Nature* 411:494-498). This mechanism may be used to down-regulate expression levels of identified genes, e.g. for treatment of or validation of relevance to disease. Antisense polynucleotides can comprise naturally-occurring nucleotides, or synthetic species formed from naturally-occurring subunits or their close homologs (see Isis Pharmaceuticals, Carlsbad, Calif.; Sequitor, Inc., Natick, Mass.). RNA molecules of interest, include but are not limited to, shRNAs or antisense RNA molecules which hybridize to the nucleotide sequences encoding cell survival proteins overexpressed in cancer cells (e.g. survivin and XIAP (Ling and Li (2004) *Biotechniques* 36:450-460; McManus et al. (2004) *Oncogene* 23:8105-8117) or multi-drug resistance genes (e.g. Stege et al. (2004) *Cancer Gene Therapy* 11:699-706).

In another embodiment, the genetic element of interest is a chimeric gene consisting of a gene that encodes a protein that traverses cell membranes, for example, VP22 or TAT, fused to a gene that encodes a protein that is toxic to tumor but not normal cells (Snyder and Dowdy (2004) *Pharm. Res.* 21:389-393).

The transposon of the invention can further comprise an expression element, located upstream from, and operably linked to, the genetic element of interest described above. The nucleic acid sequence comprising both the genetic element of interest and the expression element is referred to as an "expression cassette". An expression cassette comprising an SV40 promoter and a GFP reporter gene, for example, is represented as "SV40/GFP".

In one embodiment of the present invention, the expression element is a eukaryotic promoter, capable of driving expression of the genetic element of interest when the transposon is inserted in the proper orientation within the viral genome. Possible promoters include, but are not limited to, e.g. a traditional POL II eukaryotic promoter (e.g. E2F or hTERT (Wu et al. *Trends in Mol. Med.* (2003) 9:421-429)), a POL III promoter (e.g. U6) or a viral promoter (e.g. SV40, CMV, TK or MLP). A particularly preferred promoter is the SV40 promoter.

In another embodiment, the expression element is a eukaryotic splice acceptor sequence (Senapahty et al. (1990) *Methods Enzymol.* 183:252-278). When the transposon, comprising the splice acceptor sequence upstream from, and operably linked to, a genetic element of interest, is appropriately inserted into the viral genome, transcription of the genetic element can occur. Preferred splice acceptor sequences are the sequences SEQ ID NO: 1 (5'-TGCTAATCTTC-CTTTCTCTCTTCAGG-3'), SEQ ID NO: 2 (5'-TTTCTCTCTTCAGG-3') or SEQ ID NO: 3 (5'-CAGG-3'). A particularly preferred sequence is SEQ ID NO: 1.

In another embodiment of the present invention, the transposon further comprises restriction enzyme sites located close to the ends of the transposon and unique to the transposon, i.e. not present in the genomic DNA of the replication competent target virus. In a preferred embodiment, the restriction enzyme sites are identical. A particularly preferred restriction enzyme site is a PmeI site. The presence of these restriction enzyme sites allows facile replacement of the genetic element of interest or the expression cassette present in the originally isolated product virus (see Examples 5 and 6) and thereby permits use of one well-characterized product virus as a backbone for the creation of a series of viral vectors. Each viral vector, although derived from one product virus, can be armed with a different expression cassette and thus be used to target treatment of different diseases.

Also contemplated within the scope of the invention are further steps within the method of the invention that increase the efficiency of identification/isolation of product viruses produced by the method of the invention. For example, in one embodiment of the invention, product viruses isolated from bacteria are subjected to two rounds of infection using different eukaryotic cells, so as to increase the number of viral DNA colonies produced (see Example 4). Such additional steps are useful, but are not necessary, to the practice of the invention.

As mentioned above, the donor DNA comprising the transposon may be linear or may be a plasmid. Where the donor DNA is a plasmid, the donor DNA may further comprise an origin of replication, for example, the R6K origin of replication. A properly chosen origin of replication insures that donor plasmids will not be able to multiply in a bacterial cell chosen for amplification of product viruses. Choice of an appropriate origin of replication is well within the knowledge of one skilled in the art.

The transposon can further comprise a marker or selectable gene that is useful in the efficient isolation and/or identification of product viruses. Such a gene often provides a selective growth advantage; e.g., the gene may enhance cell viability, relieve a nutritional requirement, and/or provide resistance to a drug. Any desired marker or selectable gene can be used, including, but not limited to, genes conferring antibiotic resistance (e.g. resistance to chloramphenicol, tetracycline, ampicillin, kanamycin) or drug resistance (e.g. resistance to methotrexate or G418). The preferred selectable gene may depend on the organism being used to isolate or amplify the product viruses, e.g. antibiotic resistance when using bacterial cells, methotrexate resistance when using eukaryotic cells. Alternatively, a marker or reporter gene may encode a gene product that, by enzymatic activity, gives rise to a detection signal based on color, fluorescence, or luminescence. Many reporter genes are known to those of skill in the art and others may be identified or synthesized by methods known to those of skill in the art. Useful reporter genes include, but are not limited to, green fluorescing protein (GFP), LacZ, renilla luciferase or firefly luciferase. A particularly preferred reporter gene is GFP. Assays for measuring these proteins are well known in the art. The choice of an appropriate selection/marker gene is well within the knowledge of one skilled in the art.

Figure 1:
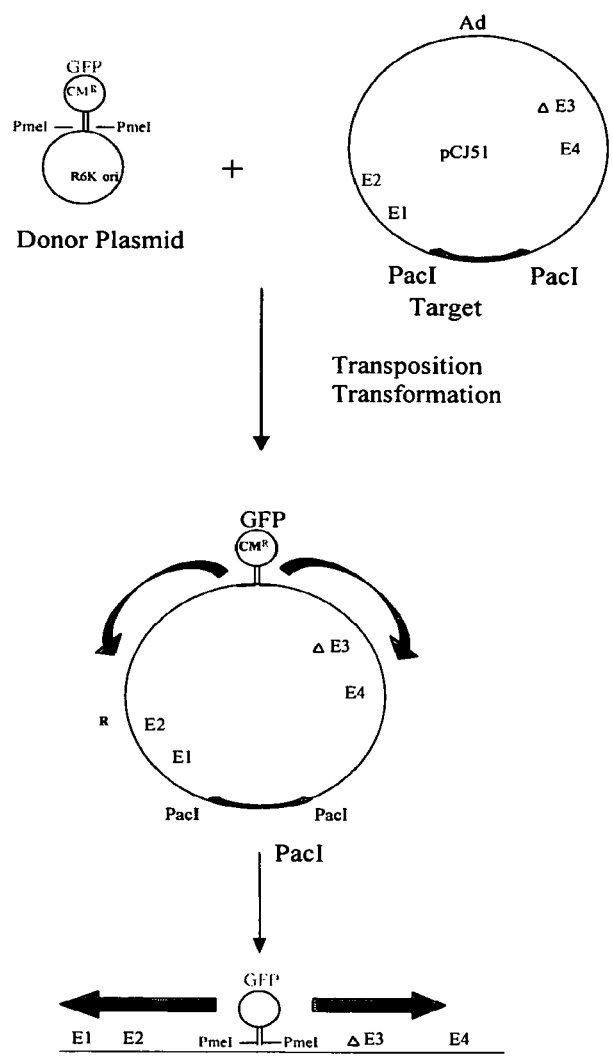
FIG. 1. Schematic of transposon-based method to identify novel insertion sites within the genome of a replication competent virus. A donor plasmid containing both an R6K origin of replication and a transposon is mixed with a plasmid (pCJ51) containing the Ad5 genome (with the E3 region deleted) flanked by two PacI restriction enzyme sites. The transposon contains a reporter gene, GFP, operably linked to an early SV40 promoter, i.e. an SV40/GFP expression cassette, and also contains a chloramphenicol resistance gene (CM$^R$). Following in vitro transposition (see Example 3), *E. coli* DH10B cells are transformed with the transposition mixture, and the transformed cells plated on chloramphenicol-containing plates. The donor plasmid, because of its R6K origin of replication, cannot grow in DH10B cells. Plating on chloramphenicol-containing media selects for those cells containing Ad5 plasmids into which a transposon has been inserted. Chloramphenicol resistant colonies are pooled and plasmid DNA extracted. The extracted DNA is digested with PacI to release linearized Ad5 genomic DNAs containing transposons inserted into various locations within the Ad5 genome. The isolated linearized Ad5 genomic DNA is transfected into a cell line of choice and individual green plaques, each containing a replication competent product virus, are picked for further characterization (e.g. insert site location, potency, etc.)

In a preferred embodiment of the invention (see Example 3; FIG. 1), the donor DNA is a plasmid comprising an R6K origin of replication and a transposon, where the transposon comprises a chloramphenicol resistance gene, as well as a GFP expression cassette, SV40/GFP, i.e. a GFP gene with an SV40 promoter operably linked to it.

Identification and Evaluation of Product Viruses.

Replication competent product viruses comprising a transposon inserted into a functional site within the viral genome generated by the method of the invention are identified and evaluated by measurement of expression of the genetic element of interest present within the inserted transposon.

Expression can be assayed in a variety of ways. If the genetic element of interest is a reporter gene, the product encoded by the reporter gene is usually detected by an intrinsic activity associated with that product. For example, the reporter gene can be chosen from firefly luciferase (deWet et al. (1987) *Proc. Natl. Acad. Sci.* 1:4154-4158), bacterial luciferase (Baldwin et al. (1984) *Biochemistry* 23:3663-3667) or alkaline phosphatase (Toh et al. (1989) *Eur. J. Biochem.* 182:231-238). Assays for these proteins are well known in the art and many kits to perform these assays are commercially available (e.g. Dual-Luciferase Reporter Assay Kit, Promega, Madison, Wis.). In one preferred embodiment, use of a reporter gene encoding GFP permits identification of product viruses as green-fluorescing plaques.

Other methods for measurement of gene expression that can be used include, but are not limited to, Southern blotting, Northern blotting to quantitate mRNA transcription (Thomas et al. (1980) *Proc. Natl. Acad. Sci. USA* 77:5201-5205), DNA analysis by dot blotting, or in situ hybridization, using an appropriately labeled probe, based on the sequences of the inserted genetic element. Alternatively, gene expression may be measured by immunological methods, such as immunohistochemical staining of cells or tissue sections, to directly quantitate the expression of a gene product using appropriately specific antibodies. Antibodies useful for immunohistochemical staining and/or assay of cell supernatants may be either monoclonal or polyclonal.

When the genetic element of interest encodes a therapeutic protein, assays that directly measure protein expression or assays which measure an activity of the expressed protein can be used to identify product viruses of potential interest. In general, assay methods that can be used to determine levels of an expressed protein in a sample derived from a host are well-known to those of skill in the art and include such assay methods as radioimmunoassays (RIA), competitive-binding assays, western Blot analysis and enzyme-linked immunoabsorbant assays (ELISA), fluorescent activated cell sorting (FACS), and surface plasmon resonance. Among these, ELISAs frequently are preferred. An ELISA assay requires having an antibody specific to the gene product of interest, preferably a monoclonal antibody. In addition, a reporter antibody generally is prepared which binds to the monoclonal antibody or is directly conjugated to the antibody. The reporter antibody is attached to a detectable reagent such as a radioactive, fluorescent or enzymatic reagent, e.g. horseradish peroxidase enzyme.

To carry out an ELISA, a sample is removed from a host and incubated on a solid support, e.g. a polystyrene dish that binds the polypeptides in the sample. Any free polypeptide binding sites on the dish are then covered by incubating with a non-specific protein such as bovine serum albumin. Next, the monoclonal antibody is incubated in the dish during which time the monoclonal antibodies attach to any product polypeptides attached to a solid support. Unbound monoclonal antibody is separated from bound antibody by washing with buffer. The reporter antibody linked to horseradish peroxidase is placed in the dish resulting in binding of the reporter antibody to any monoclonal antibody bound to the gene product of interest. Unattached reporter antibody is then washed out. Reagents for peroxidase activity, including a colorimetric substrate are then added to the dish. Immobilized peroxidase, linked to the product protein through the primary and secondary antibodies, produces a colored reaction product. The amount of color developed in a given time period indicates the amount of product polypeptide present in the sample. Quantitative results typically are obtained by reference to a standard curve.

A competition assay may be employed wherein antibodies specific to the product protein are attached to a solid support and labeled product protein and a sample derived from the host are passed over the solid support and the amount of label detected attached to the solid support correlated to a quantity of product protein in the sample.

These and other assays are described, among other places, in Hampton et al. (*Serological Methods, a Laboratory Manual*, APS Press, St Paul, Minn., 1990) and Maddox et al. (*J. Exp. Med.* 158:12111, 1983).

Expression of shRNA or antisense RNA expression can be measured through measurement of the expression of, or activity of, the target message; i.e. a reduction in either of these measurements would indicate production of the desired RNA molecule.

Replacement of Genetic Element of Interest within a Product Virus

One advantage of the present invention is the potential to use an isolated and characterized product virus of the invention as a gene therapy vector for more than one therapeutic indication. This is accomplished by incorporating the ability to easily exchange the genetic element of interest or expression cassette present within the transposon of the originally isolated product virus with a different genetic element of interest or expression cassette. Transposons useful in the present invention, therefore, further comprise unique enzyme restriction sites; i.e. sites not present in the starting viral genome, located close to the ends of the transposon. Presence of these restriction enzyme sites allows facile replacement of the original genetic element of interest or expression cassette present in an isolated product virus with a different genetic element of interest or expression cassette. In a preferred embodiment, the restriction enzymes sites are blunt-ended restriction enzyme sites, allowing insertion of a replacement genetic element of interest or expression cassette in both possible orientations within the product viral genome. It has been shown that expression levels from therapeutic genes placed within the replicating virus can vary depending on the viral sequences flanking the gene and on the orientation of the gene within the viral genome (Schneider et al. (1989) *J. Gen. Virol.* 70: (Pt 2) 417-427; Mittal et al. (1995) *Virology* 210: 226-230) so it is useful to be able to generate product viruses containing genetic elements (or expression cassettes) inserted in both directions for evaluation.

In a particularly preferred embodiment, the restriction enzyme sites are identical. A particularly preferred restriction enzyme site is the PmeI restriction enzyme site; however, choice of enzyme restriction sites is well within the knowledge of one skilled in the art (see Examples 5 and 6).

The replacement genetic element of interest, whether alone or within an expression cassette can be any genetic element; however, there is a limitation on the size of the insert which can be used and still allow proper viral packaging (see, for example, Bett et al (1993) *J. Virol.* 10:5911-5921).

Figure 4A:
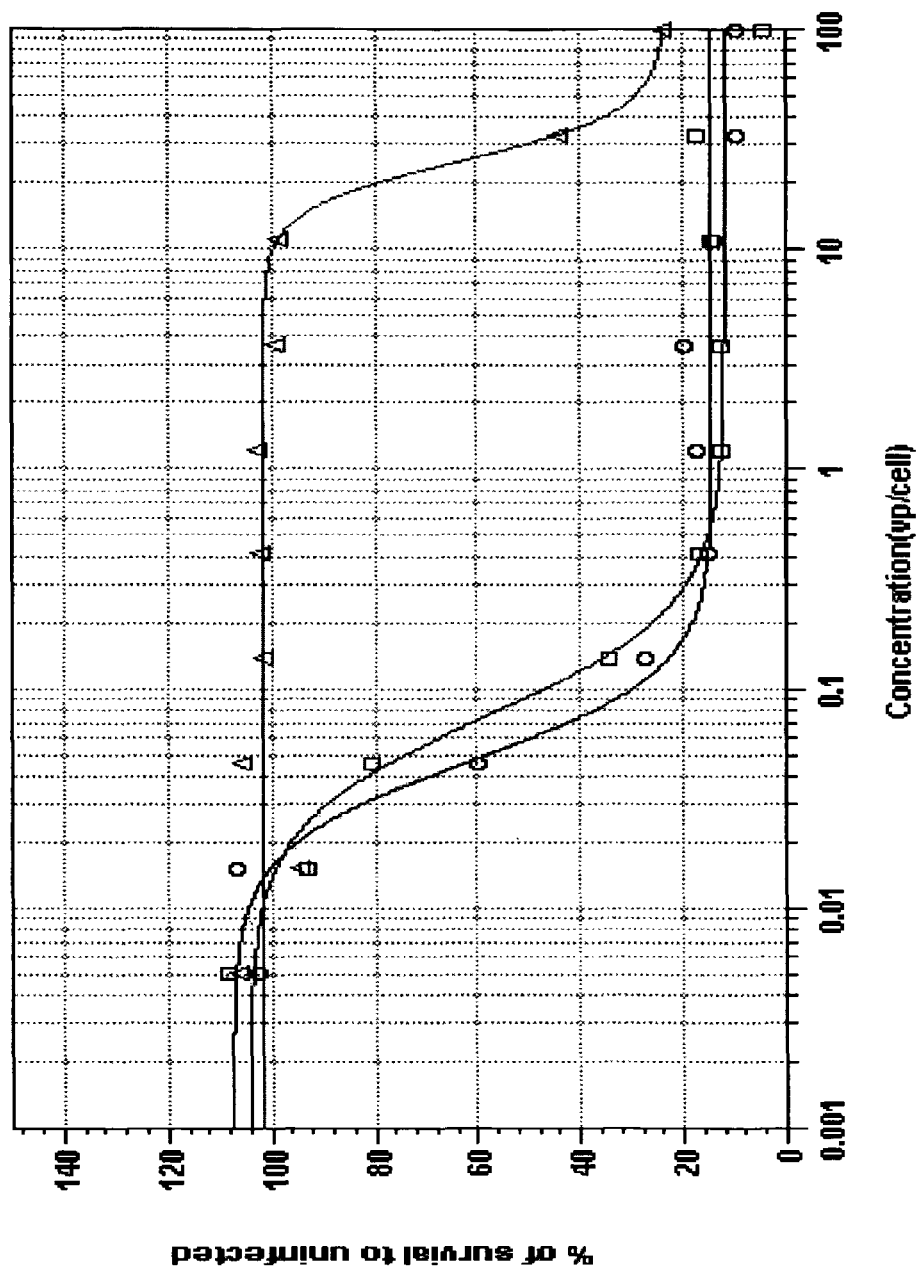
FIG. 4. Potency of Ad5-viral isolates containing transposons. MTT assays were performed in HT29 cells comparing the potency of the original Ad5 virus (AdCJ51) and a number of transposon-containing viruses, as described below. The transposon-containing viruses, Ad5/PL11 and Ad5/PL29, contain the SV40/GFP expression cassette inserted within the Ad5 genome, with GFP expression oriented leftwards or rightwards in the Ad5 genome, respectively (see arrows in FIG. 3, Example 4). In other viruses tested, the original expression cassette (SV40/GFP) present in the Ad5/PL11 and Ad5/PL29 viruses was replaced by a CMV/Luc, TK/RL or CMV/LacZ expression cassette as described in Examples 5 to 7.
Figure 4B:
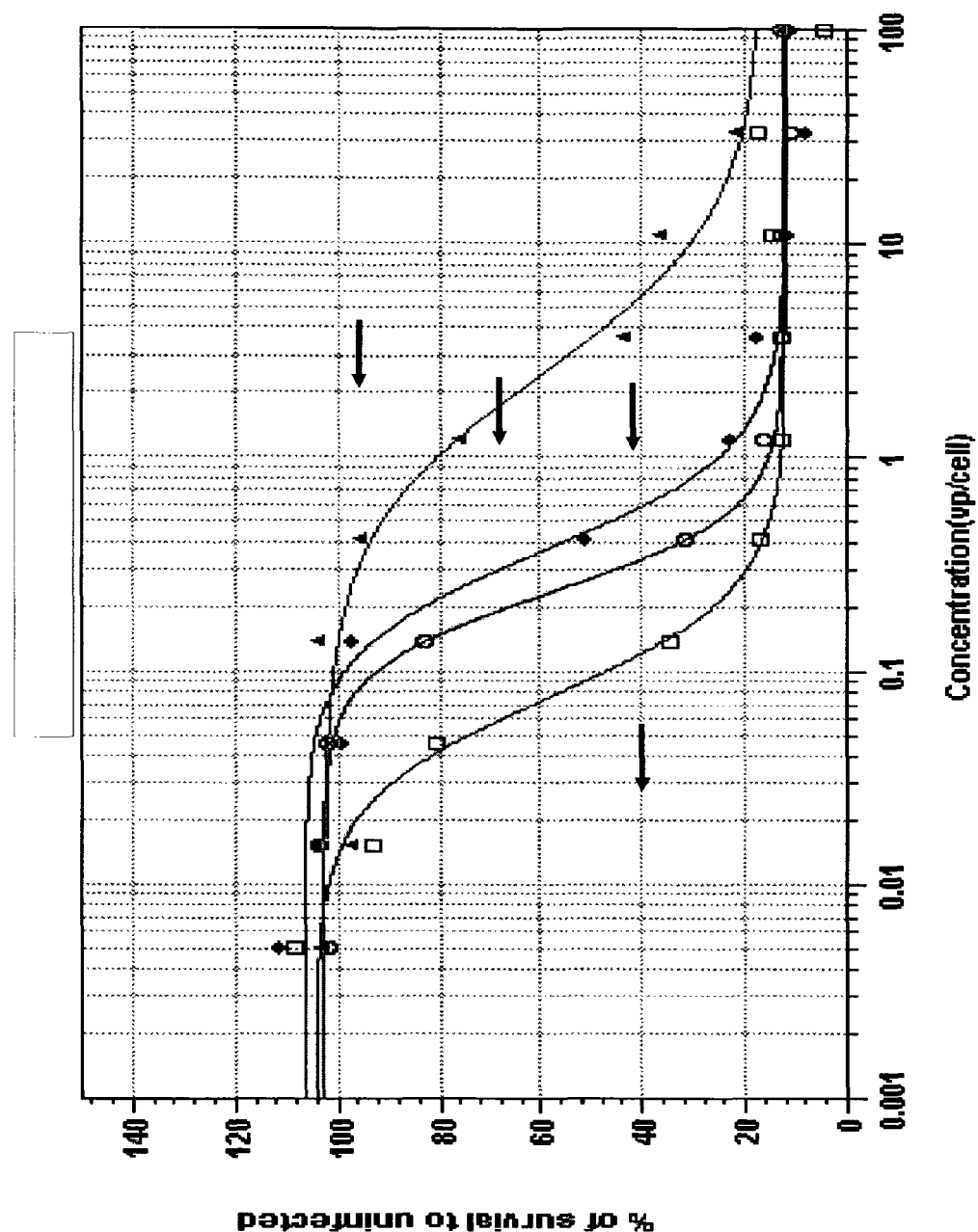
Figure 4C:
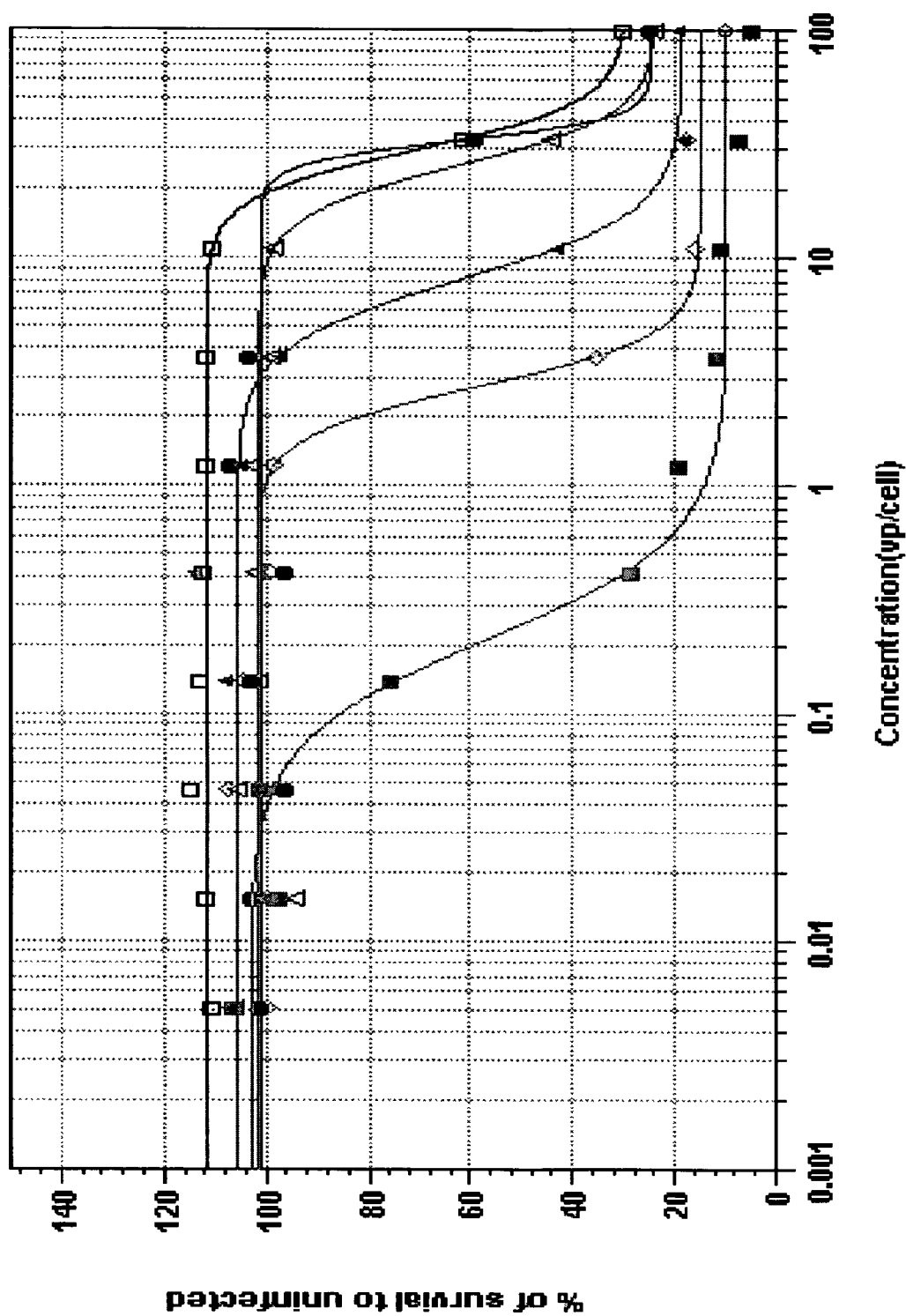

Table 1 contains the results of an experiment showing replacement of an SV40/GFP expression cassette present within two isolated product viruses, identified as PL29 and PL11 (see Example 5). The SV40/GFP expression cassette is replaced with other expression cassettes, i.e. TK/RL, CMV/LUC or CMV/LacZ (see Examples 6), allowing isolation of new replication competent product viruses containing the expression cassettes oriented in both directions within the PL29 and PL11 genomes. FIG. 4 demonstrates the difference in potency among the various replication competent product viruses generated by these substitutions.

Therapeutic Activity Measurements

Replication competent product viruses of the invention are evaluated for their therapeutic utility using in vitro or in vivo systems designed to model a particular disease or condition. Elegant models now exist for some of the major cancer indications, e.g. prostate cancer (Russell and Voeks (2003) *Methods Mol. Med.* 81:89-112; Powell et al. (2003) *Current Drug Targets* 4:263-279), bone metastasis (Rosol et al. (2004) *Cancer Treat. Rep.* 118:47-81), angiogenesis (Mg et al. (2000) *J. Neurooncol.* 50:89-98; Hanahan et al. (1996) *Eur. J. Cancer* 32A:2386-2393) and these can be complemented, in some cases, by spontaneous tumor models in dogs and cats (Hansen and Khanna (2004) *Eur. J. Cancer* 40: 858-880).

Utility in the treatment of malignancy can be examined by measurement of the lytic potential of a product virus in tumor cells derived from tissues of interest as therapeutic targets. Tumor cell lines useful for testing such viruses may include, but are not limited to, colon cell lines, including but not limited to, DLD-1, HCT116, HT29, LS1034 and SW48 cell lines; prostate cell lines, including but not limited to, DU145 and PC-3 cell fines; pancreatic cell lines, including but not limited to, the Panc-1 cell line; breast tumor cell lines, including but not limited to, the MDA231 cell line and ovarian cell lines, including but not limited to, the OVCAR-3 cell line. Hemopoietic cell lines include, but are not limited to, the Raji and Daudi B-lymphoid cells, K562 erythroblastoid cells, U937 myeloid cells, and HSB2 T-lymphoid cells. Any other tumor cell lines that are available can be used in evaluating and identifying replication competent viruses of the invention for the treatment of neoplasia.

The cytolytic activity of the replication competent viruses of the invention can be determined in representative tumor cell lines and the data converted to a measurement of potency, with an adenovirus belonging to subgroup C, preferably Ad5, being used as a standard (i.e. given a potency of 1). A preferred method for determining cytolytic activity is an MTT assay (see Example 7, FIG. 4).

The therapeutic index of a replication competent virus of the invention in a particular tumor cell line can be calculated by comparison of the potency of the given virus in a tumor cell line with the potency of that same virus in a non-cancerous cell line. Preferred non-cancerous cell lines are SAEC cells, which are epithelial in origin, and HuVec cells, which are endothelial in origin. These two cell types represent normal cells from which organs and vasculature, respectively, are derived, and are representative of likely sites of toxicity during viral therapy, depending on the mode of delivery of the virus. However, practice of the invention is not limited to the use of these cells, and other non-cancerous cell lines (e.g. B cells, T cells, macrophages, monocytes, fibroblasts) may also be used.

The replication competent viruses of the invention can be further evaluated for their ability to target neoplastic cell growth (i.e. cancer) by their capacity to reduce tumorigenesis or neoplastic cell burden in nude mice harboring a transplant of neoplastic cells, as compared to untreated mice harboring an equivalent neoplastic cell burden.

Evaluation of the replication competent viruses of the invention can also be performed using primary human tumor explants (Lam et al. (2003) *Cancer Gene Therapy*; Grill et al. (2003) *Mol. Therapy* 6:609-614), which provide test conditions present in tumors that cannot normally be produced using the tumor xenograft studies.

Therapeutic Utility

The replication competent viruses generated by the method of the invention are useful in gene therapy.

Pharmaceutical Compositions and Administration

The present invention also relates to pharmaceutical compositions that comprise the replication competent viruses of the invention, formulated for therapeutic administration to a patient. For therapeutic use, a sterile composition containing a pharmacologically effective dosage of virus is administered to a human patient or veterinary non-human patient for treatment, for example, of a neoplastic condition. Generally, the composition will comprise about $10^{11}$ or more adenovirus particles in an aqueous suspension. A pharmaceutically acceptable carrier or excipient is often employed in such sterile compositions. A variety of aqueous solutions can be used, e.g. water, buffered water, 0.4% saline, 0.3%-glycine and the like. These solutions are sterile and generally free of particulate matter other than the desired adenoviral vector. The compositions may contain pharmaceutically acceptable auxiliary substances as required to approximate physiological conditions such as pH adjusting and buffering agents, toxicity adjusting agents and the like, e.g. sodium acetate, sodium chloride, potassium chloride, calcium chloride, sodium lactate, etc. Excipients that enhance infection of cells by adenovirus may be included. (see U.S. Pat. No. 6,392,069)

Viruses of the invention may also be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions is encapsulated in liposomes or immunoliposomes. For example, a suspension of adenoviral virions can be encapsulated in micelles to form immunoliposomes by conventional methods (U.S. Pat. No. 5,043,164, U.S. Pat. No. 4,957,735, U.S. Pat. No. 4,925,661; Connor and Huang, (1985) *J. Cell Biol.* 101: 581; Lasic D. D. (1992) *Nature* 355: 279; Novel Drug Delivery (eds. Prescott and Nimmo, Wiley, New York-, 1989); Reddy et al. (1992) *J. Immunol.* 148:1585). Immunoliposomes comprising an antibody that binds specifically to a cancer cell antigen (e.g., CALLA, CEA) present on the cancer cells of the individual may be used to target virions to those cells (Fisher (2001) *Gene Therapy* 8:341-348).

Viral Therapy

The viruses of the invention, or pharmaceutical compositions thereof, can be administered for therapeutic treatment of neoplastic disease or cancer. In therapeutic applications, compositions are administered to a patient already affected by the particular neoplastic disease, in an amount sufficient to cure or at least partially arrest the condition and its complications. An amount adequate to accomplish this is defined as a "therapeutically effective dose" or "efficacious dose". Amounts effective for this use will depend upon the severity of the condition, the general state of the patient, and the route of administration.

For example, but not by way of limitation, a human patient or non-human mammal having a solid or haemotologic neoplastic disease, (e.g. pancreatic, colon, ovarian, lung, or breast carcinoma, leukemia or multiple myeloma) may be treated by administering a therapeutically effective dosage of an appropriate adenovirus of the invention, i.e. one which has been shown to have an improved therapeutic index for that tissue type. A preferred chimeric adenovirus for the treatment of colon cancer would be the adenovirus ColoAd1 (SEQ ID NO: 22). Suspensions of infectious adenovirus particles may be delivered to neoplastic tissue by various routes, including intravenous, intraperitoneal, intramuscular, subdermal, and topical. An adenovirus suspension containing about $10^3$ to $10^{12}$ or more virion particles per ml may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g. a breast tumor), enema (e.g., colon cancer), or catheter (e.g., bladder cancer). Other routes of administration may be suitable for carcinomas of other origins, i.e. inhalation as a mist (e.g., for pulmonary delivery to treat bronchogenic carcinoma, small-cell lung carcinoma, non-small cell lung carcinoma, lung adenocarcinoma, or laryngeal cancer) or direct application to a tumor site (e.g., bronchogenic carcinoma, nasopharyngeal carcinoma, laryngeal carcinoma, cervical carcinoma).

Viral therapy using the replication competent viruses of the instant invention may be combined with other antineoplastic protocols, such as conventional chemotherapy or x-ray therapy to treat particular cancers. Treatment can be concurrent or sequential. A preferred chemotherapeutic agent is cisplatin, and the preferred dose may be chosen by the practitioner based on the nature of the cancer to be treated, and other factors routinely considered in administering cisplatin. Preferably, cisplatin will be administered intravenously at a dose of 50-120 mg/m$^2$ over 3-6 hours. More preferably it is administered intravenously at a dose of 80 mg/m$^2$ over 4 hours. A second preferred chemotherapeutic agent is 5-fluorouracil, which is often administered in combination with cisplatin. The preferred dose of 5-fluorouracil is 800-1200 mg/m$^2$ per day for 5 consecutive days.

Viral therapy using the replication competent viruses of the instant invention as vectors may also be combined with other genes known to be useful in viral based therapy. See U.S. Pat. No. 5,648,478.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

The present invention is further described by the following examples, which are illustrative of specific embodiments of the invention, and various uses thereof. These exemplifications, which illustrating certain specific aspects of the invention, do not portray the limitations or circumscribe the scope of the disclosed invention.

Unless otherwise indicated, the practice of the present invention employs conventional techniques of cell culture, molecular biology, microbiology, recombinant DNA manipulation, immunology science, which are within the skill of the art. Such techniques are explained fully in the literature. See, e.g. Cell Biology: a Laboratory Handbook: J. Celis (Ed).Academic Press. N.Y. (1996); Graham, F. L. and Prevec, L. Adenovirus-based expression vectors and recombinant vaccines. In: Vaccines: New Approaches to Immunological Problems. R. W. Ellis (ed) Butterworth. Pp 363-390; Grahan and Prevec Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109-128, 1991; Sambrook et al. (1989), Molecular Cloning, A Laboratory Manual, 2nd ed., Cold Spring Harbor Laboratory Press; Sambrook et al. (1989), and Ausubel et al. (1995), Short Protocols in Molecular Biology, John Wiley and Sons.

EXAMPLES

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., Molecular Cloning: A Laboratory Manual, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation and delivery, and treatment of patients. Methods for the construction of adenoviral mutants are generally known in the art. See, Mittal, S. K., Virus Res., 1993, vol: 28, pages 67-90; and Hermiston, T. et al., Methods in Molecular Medicine: Adenovirus Methods and Protocols, W. S. M. Wold, ed, Humana Press, 1999.

The following examples are offered by way of illustration and are not intended to limit the invention in any way.

Example 1

Construction of Donor Plasmids

A. Donor plasmid containing a transposon with an SV40/GFP expression cassette. The oligonucleotides GER82 (5'-AAATGTGGCCGGCCACTGATTCCACG-TAGTGGTCAGGTA-3'; SEQ ID NO: 4) and GER83 (5'-CTAGTACCTGACCACTACGTGGAATCAGTGGCCGGC CACATTT-3'; SEQ ID NO: 5) were annealed and cloned into the SwaI/SpeI digested pGPS4 plasmid (New England Biolabs, Beverly, Mass., USA), adding FseI and DraIII restriction sites to pGPS4 in the order SwaI-FseI-DraIII-SpeI, producing the plasmid pGER57. Annealing of oligonucleotides GER72 (5'-GGAATTGGCCGGCCAT ATCCGC-3'; SEQ ID NO: 6) and GER73 (5'-GGATATGGCCGGCCAAT-TCCGC-3'; SEQ ID NO: 7) and ligation to a SacII digested plasmid pQBI25-fPA (Q-Biogene, Carlsbad, Calif., USA) created plasmid pGER54, which contains a unique FseI site immediately 5' of the sgGFP coding sequence. The SV40 promoter/enhancer was PCR amplified from phRL-SV40 (Promega, Madison, Wis., USA) with oligonucleotides GER94 (5'-CATGGATGGCCGGCCGCTGTGGAATGT-GTGTC A G-3'; SEQ ID NO: 8) and GER95 (5'-TCAG-TAGCTAGCCATGGTGGCTAAGAGCTG-TAATTGAACTGG-3'; SEQ ID NO: 9) and restriction enzyme digested to create a fragment with the following features: FseI-SV40 promoter/enhancer-small IVS-NheI. This fragment was cloned into the FseI/NheI digested pGER54 plasmid to create plasmid pGER59, which contains a transcription unit bounded by FseI and DraIII in which the sgGFP gene is driven by the SV40 promoter/enhancer. This transcription unit was then cloned into the FseI/DraIII digested pGER57 to result in a plasmid, pGER98, which contains a chloramphenicol gene and SV40-sgGFP transcription unit within the Tn7 transposon.

Plasmids pGPS4, pGER57 and pGER98 have the R6K origin of replication and are unable to grow in ordinary lab strains of E. coli such as DH5a which are pir– (Kolter et al. (1978) Cell 15:1199-1208 (1978); Metcalf et al. (1994) Gene 138:1-7). For transformation and growth of these plasmids, a desired amount of DNA or ligation mixture was added to 20 ul electrocompetent E. coli TransforMax EC100™ pir+ cells (Epicentre, Madison, Wis., USA) in a chilled microcentrifuge tube. The cell/DNA mixture was then transferred to a chilled cuvette and electroporated at the settings recommended by the manufacturer. Immediately after electroporation, the cell/DNA mixture was transferred to 1 ml of SOC medium (Invitrogen, Carlsbad, Calif., USA) and incubated at 37° C. for 1 hour with shaking. The desired number of cells was plated on CM$^R$ LB agar plates for growth of colonies.

B. Donor plasmids containing transposons with splice acceptor/GFP expression cassettes. Plasmid pGER54 containing sgGFP (see above, this Example) was digested with FseI and NheI, and ligated to two sets of oligos, GER88 (5'-CCTTTCTCTCTTCAGGCCGCCATGG-3'; SEQ ID NO: 10) and GER99 (5'-GTTCTGGATCCGTGAGTCAA-CAGGAAAGTTCC-3'; SEQ ID NO: 11), which when annealed give a FseI-SA-NheI fragment, and GER100 (5'-CCTGCTAATCTTCCTTTCTCTCTTCAG-GCCGCCATGG-3'; SEQ ID NO: 12) and GER101 (5'-CTAGCCATGGCGGCCTGAAGAGAGAAAGGAAGATT AGCAGGCCGG-3'; SEQ ID NO: 13), which when annealed give an FseI-BPS-NheI fragment, resulting in plasmids pGER99 and pGER100, respectively. These latter two plasmids were digested with FseI and DraIII and ligated to FseI/DraIII digested pGER57 (see above, this Example) to result in plasmids pGER111, containing a transposon with the splice acceptor sequence, SEQ ID NO: 1 and pGER112, containing a transposon with the branch-point splice acceptor sequence, SEQ ID NO: 2.

Example 2

Generation of a Starting Plasmid (pCJ51) Comprising an Ad5 Genome

The left end of Ad5 was introduced into pAdEasy (Stratagene, La Jolla, Calif., USA) by homologous recombination. The ScaI-BstZ171 fragment of pTG3602 (Chartier et al, 1996) was co-transfected along with ClaI-linearized pAdEasy into BJ5183 bacteria (Stratagene, La Jolla, Calif., USA). The resulting recombinant plasmid was named pCJ38. The SalI fragment of pAdEasy corresponding to Ad5 nucleotides 9841-16746 was sub-cloned into the SalI site of pBluescript-KS+ (Stratagene, La Jolla, Calif. 92037, USA). The PmeI site of the resulting pCJ36 was then mutated using the CJ23-23r pair of oligonucleotides with annealed double stranded sequence as follows: 5'-CCGGCGGCAGAA-GATCCC CTCGTTGCACA[GC*TTAAAC]AGCGAG-GAGGAGCGCATTTTGCGCTA-3 (SEQ ID NO: 14). The PmeI site is bracketed and the asterisk designates the T to C point mutation that destroys the PmeI site without disturbing the IIIa ORF. Annealed oCJ23-23r was co-transfected along with PmeI-linearized pCJ36 into BJ5183 and pCJ39 was obtained by homologous recombination. Finally, the PmeI-SalI fragment of pCJ39 was re-introduced into pCJ38 by homologous recombination into the BJ5183 bacteria after linearization of the latter plasmid with PmeI. The plasmid containing the PacI-flanked, E3-deleted, and Pme$^-$ Ad5 genome was named pCJ51.

Example 3

Transposition of the sgGFP Transposon from pGER98 to pCJ51

The in vitro transposition components of the GPS™-LS Linker Scanning System from New England Biolabs (Beverly, Mass., USA) were utilized as described in the kit, as follows. The transposon donor plasmid (pGER98, 0.04 ug) was mixed with TnsABC (1 ul) and the target Ad plasmid (pCJ51, 0.16 ug) and incubated for 10 minutes at 37° C. Start solution was added, incubated for 1 hour at 37° C., and heated at 75° C. for 10 minutes, for a final volume of 20 ul. One ul of this reaction mixture resulted in approximately 5000 chloramphenicol resistant colonies following electroporation to DH10B electrocompetent cells (Invitrogen, Carlsbad, Calif., USA).

Transposition of the splice acceptor transposons were performed in the same way.

Example 4

Identification of Transposon Insertion Sites within the Ad5 Genome

Chloramphenicol resistant colonies (see above) were pooled (about 10,000 colonies per pool) and plasmid DNA was extracted using Qiagen (Valencia, Calif., USA) endo-free plasmid extraction kits. Five ug of PacI-digested plasmid DNA was transfected into one 10 cm dish of HEK 293 cells by the calcium phosphate method (Invitrogen, Carlsbad, Calif., USA). After overnight incubation, 15 ml of 2% agar (2% agar in 2% FBS DMEM plus penicillin/Streptomycin) was then added to the cells. Four or five days later, another 10 ml of 2% agar was added. After 10 days to 3 weeks incubation, green plaques were isolated, and serial dilutions ($10^{-3}$ to $10^{-9}$) of these plaques were used to infect A549 cells plated in 6-well plates. After 30 minutes, 2 ml of 2% agar were added to the cells. Three to four days later another layer of agar was added, and green plaques from the highest dilutions were picked and amplified (6 from 60 plaques). Viral DNA was extracted from the cells using the HIRT method (Hirt B. (1967) *J. Biol.* 26:265-369) as follows. A549 cells were plated in 10 cm dishes and infected with 100 ul to 200 ul of viral CPE stock after overnight culture. After 16 to 48 hours the cells were lysed with 1 ml of HIRT extraction buffer (0.6% SDS, 0.5 nM EDTA and 1 nM Tris pH 7.5) and rocked slowly in a shaker for 15 minutes, after which 250 ul of 5M NaCl was added followed by storage overnight at 4° C. The cell lysate was then microcentrifuged for 30 minutes at 4° C. followed by proteinase K digestion (final concentration: 500 ug/ml) for 2-3 hours at 37° C. After 1× phenol-chloroform and 1× chloroform extraction of the cell lysate, viral DNA was precipitated by 2 volumes of EtOH and $\frac{1}{10}$ volume of 3M NaOAc pH 5.2. The DNA precipitate was then washed with 70% alcohol and resuspended in 100 ul of TE buffer.

Figure 2:
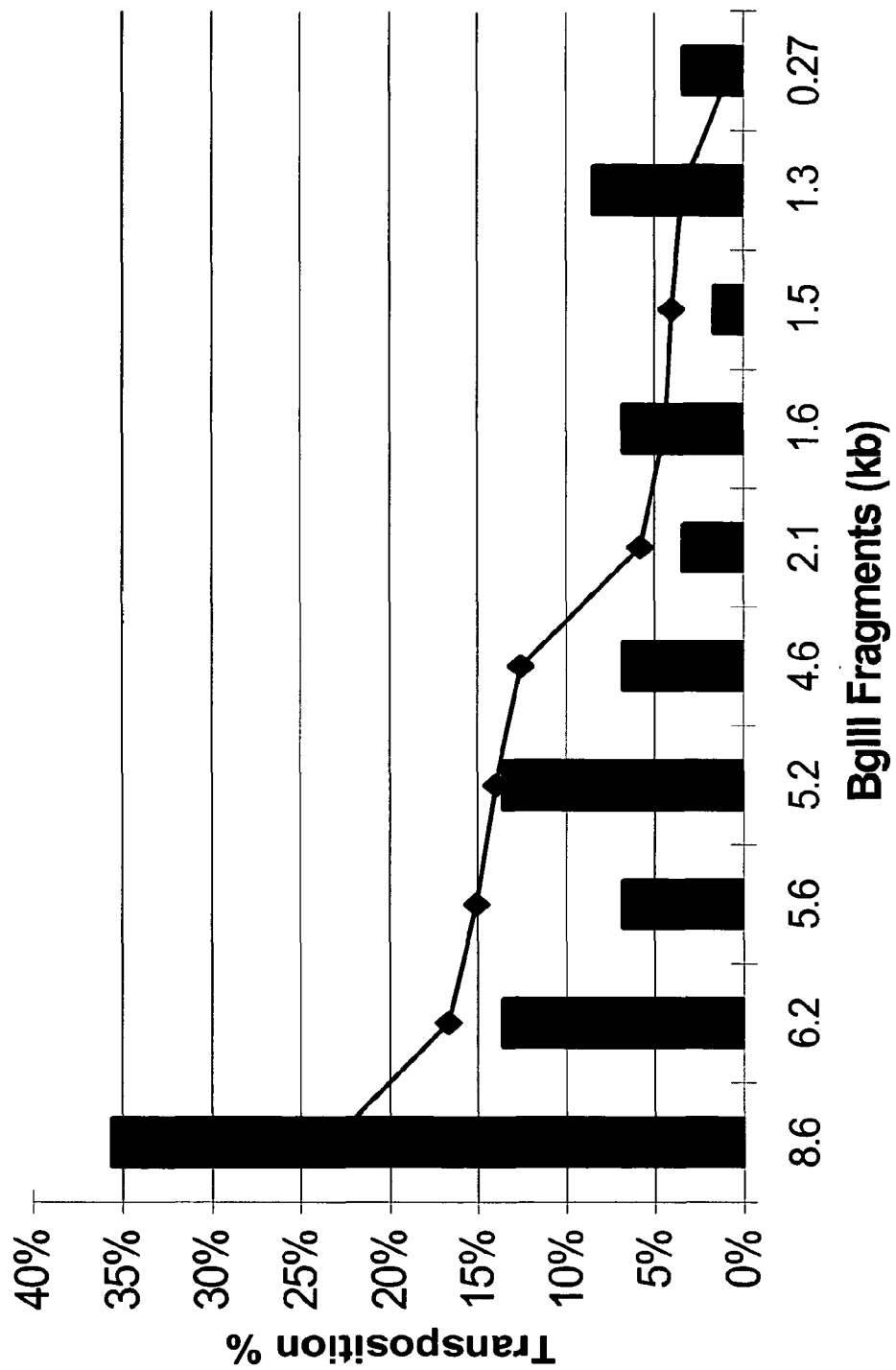
FIG. 2. Distribution of transposon insertions within the Ad5 genome Plasmid DNA containing inserted transposons, isolated from 60 chloramphenicol-resistant colonies, was digested with Bgl II and the resulting DNA fragments were analysed on 1% agarose gels. The Bgl II restriction fragments of the Ad5 containing plasmid, pCJ51, range in size from 8.6 kb (which includes the entire plasmid portion) to 0.27 kb. The transposon contains a Bgl II restriction site within 32 bp of the right end of the transposon. Therefore, insertion into any Bgl II fragment will result in loss of that fragment and the appearance of two new fragments, the sum of which will total the fragment plus 3.1 kb (the size of the transposon). The fragment sizes will vary depending upon the site of insertion within the fragment, and on the orientation of the inserted transposon. The percentage of insertions within each fragment is shown on the y-axis, while the continuous line indicates the percentage predicted if insertion is non-biased (see Example 4).

The viral DNA was initially digested with Bgl II to identify the Bgl II fragment containing the inserted transposon (see FIG. 2). In order to define the exact insertion site, PCR primers capable of amplifying approximately 3 kb of the Ad5 genome in overlapping segments within and/or flanking the identified Bgl II fragments were used to amplify the inserted transposons flanked by Ad5 DNA. The PCR fragments were sequenced using primers originating within the transposon and oriented toward the Ad5 DNA at each end of the transposon. For all Ad-transposon genomes examined in this manner, the two sequences were found to indicate the identical position and orientation of the transposon insertion for any given Ad isolate. Results are shown in FIG. 3.

Identification of the insertion sites for transposons comprising the splice acceptor sequences SEQ ID NO: 1 (SA) or SEQ ID NO: 2(BPS) were done in the same way (see FIG. 5).

Example 5

Replacement of Genetic Elements of Interest within Ad5/PL11 and Ad5/PL29

Two plasmids, Ad5/PL11 and Ad5/PL29, which contain replication competent Ad5 viruses containing transposons comprising the SV40/GFP expression cassette (see Example 4) were used to examine the facility with which the original SV40/GFP expression cassette could be replaced with different expression cassettes.

A. Expression cassette construction. Three reporter gene expression cassettes, each of which contain a reporter gene under the control of a promoter, were constructed as follows.

The CMV/LacZ expression cassette (LacZ gene driven by the CMV promoter) was PCR amplified with primers (5'-AGCTGTTTAAACCGATGTACGGGCCAG-3' (SEQ ID NO: 15) and 5'-TGACGTTTAAACTAGAAGGCACAGTCGAGGC-3' (SEQ ID NO: 16)) using pcDNA3.1/LacZ/hygro (Invitrogen, Carlsbad, Calif., USA) as template. The TK/RL (Renilla luciferase gene driven by TK promoter) expression cassette was excised from the phRUTK vector (Promega, Madison, Wis., USA) with Bgl II and BamHI restriction endonucleases and then blunt-ended with Klenow fragment. To construct the CMV/Luc expression cassette (firefly luciferase gene driven by the CMV promoter), two oligonucleotides (5'-CTAGCGAATTCGGTACCACGCGTCTCGAGGCCAC-3' (SEQ ID NO: 17) and 5'-CATGGTGGCCTCGAGACGCGTGGTACCGAATTCG-3' (SEQ ID NO: 18)) were annealed and inserted into the pGL3Basic plasmid (Promega, Madison, Wis., USA) digested with Nhe I/Nco I, resulting in plasmid pGL3BasicI that contains a convenient multiple cloning site (Nhe I, EcoR I, Kpn I, Mlu I, Xho I and Nco I) at the 5' end of the firefly luciferase gene. The firefly luciferase gene was excised with Nhe I and Xba I from pGL3BasicI and cloned into Nhe I/Xba I digested phRL-CMV (Promega) to result in the pCMV/Luc plasmid. The CMV/Luc cassette was then excised from this plasmid with Bgl II and BamH I and blunt-ended for cloning into the Pme I sites of Ad5/PL11 and Ad5/PL29.

B. Expression cassette replacement. The blunt-ended expression cassettes (CM/LacZ, TK/RL or CMV/Luc) were cloned into the transposon insertion sites within the Ad5/PL11 and Ad5/PL29 viral DNA, using the PmeI restriction sites present near both ends of the inserted transposon. HIRT extracted or CsCl purifed Ad5/pPL11 or Ad5/PL29 DNA was digested with Pme I to remove all but 15 bp of the 3.1 kb transposon. The three reporter expression cassettes were each blunt-end ligated to PmeI-digested viral DNA using T4 DNA ligase (rapid ligation kit from Epicentre, Madison, Wis., USA). The mass ratio of the expression cassette fragment to viral DNA was 1:10. The ligation mixture was transfected into HEK 293 cells using the calcium phosphate method. After 10 days to two weeks, non-green viral plaques were picked and used to infect A549 cells to test for reporter gene expression. LacZ expression was detected by the In Situ β-Gal Staining Kit (Stratagene, La Jolla, Calif., USA). Expression of firefly or renilla luciferase was measured by the Dual-Luciferase reporter assay kit (Promega, Madison, Wis., USA). Reporter-gene expression positive plaques were then subjected to a second round of plaque assays in A549 cells. Plaques were picked from the highest dilution wells and reporter gene expression was verified.

Example 6

Identification of Insertion Orientations of Reporter Expression Cassettes

Since PmeI is a blunt-end cutter, the blunt-ended reporter expression cassettes can be inserted in both orientations. The orientation was identified by conducting two separate PCR reactions with the Ad/expression cassette viral DNA as the template. A primer common to both reactions was a reverse primer from the given expression cassette (not shown). The second primer for each reaction was one of the two primers from the set of Ad primers that originally identified the insertion site (see above under "Identification of transposon insertion sites on Ad5 genome"). Only one of the PCR fragments can result in a PCR fragment, which therefore defines the direction of orientation of insertion of the expression cassette in the Ad genome. The results are shown in Table 1.

TABLE 1

| Virus name | Total clones | # Positive clones | Orientation → | Orientation ← |
|---|---|---|---|---|
| → | | | | |
| PL29/TK/RL | 12 | 9 | 5 | 4 |
| CMV/Luc | 22 | 15 | 13 | 2 |
| CMVLacZ | 27 | 5 | 5* | 0 |
| ← | | | | |
| PL11/TK/RL | 12 | 4 | 0 | 4 |
| CMV/Luc | 2 | 2 | 0 | 2 |
| CMV/LacZ | 13 | 2 | 0 | 2 |

Example 7

Viral Propagation and Potency Measurement

Human embryonic kidney cell line HEK 293 cells and human epithelial lung carcinoma A549 cells were obtained from ATCC. Both cell lines were maintained in DMEM with 10% FBS and 0.1 nM nonessential amino acid (NEAA). For the viral infection, DMEM with 2% FBS, 0.1 nM NEAA and 1% penicillin/streptomycin was used. Viral propagation was performed as described and viruses were quantitated using a TMAE column (Shabram et al. (1997) *Human Gene Therapy* 8:453) or using the Adeno-X™ Rapid Titer Kit (Clontech, Palo Alto, Calif., USA. The viruses ability to successfully replicate, lyse and spread was measured by using a modification of the MTT assay (Shen et al. 2003 J. Virology 77:2640-2650). The MTS assay (Promega, CellTiter 96® Aqueous Non-Radioactive Cell Proliferation Assay) was used in place of the MTT assay since conversion of MTS by cells into aqueous, soluble formazan reduces time and eliminates the use of a volatile organic solvent associated with the MTT assay.

To perform the assay, cells were seeded at a defined density for each tumor cell line that generated a confluent monolayer within 24 hr. These densely seeded cells were allowed to grow for 2 additional days prior to exposure to the test virus(es). Infections of both tumor and primary normal cells were carried out in quadruplicate with serial three fold dilutions of the viruses starting at a particle per cell ratio of 100 and ending at a particle per cell ratio of 0.005. Infected cells were incubated at 37° C. and the MTS assay was performed at the time points indicated for the individual primary cells or tumor cell lines. Mock-infected cells served as negative controls and established the 100% survival point for the given assay.

Example 8

RACE Analysis of the Splice Acceptor Clones

To determine the identity of the internal viral promoters, total RNA extracted from cells infected with selected viral clones containing insertions of splice acceptor transposons were used as templates for PCR amplification using primers appropriate for RACE analysis. The GFP gene specific primer is 5'-GGCCATGGAACAGGCAGTTTGCCAGTAGTGC-3' (SEQ ID NO: 19). The 10 Universal Primer A Mix (UPM) used was from the BD SMART™ cDNA Amplification Kit from BD Biosciences (Palo Alto, Calif.; Catalog #634914), which included primers 5'-CTAATACGACTCACTATAGGGCAAGCAGTG-3' (SEQ ID NO: 20) and 5'-TAATAC- GACTCACTATAGGGC-3' (SEQ ID NO: 21). Amplified DNA fragments were isolated from agarose gels, cloned into the appropriate vector from the kit and submitted for DNA sequencing. The resulting sequence of the RACE fragment was compared to the known sequence of Ad5 in order to determine those regions of the adenovirus and transposon DNA on the RACE fragments, enabling identification of the promoter and splicing used to create mRNA containing the GFP gene.

Example 9

Generation of ColoAd1/PL30/TK/TK and its In Vitro Cytotoxicity in the Presence and Absence of Ganciclovir (GCV)

ColoAd1 (SEQ ID NO: 22) was introduced into plasmid pL30/TK/TK by the methods given in Example 2. This plasmid was then used to produce replication competent product viruses comprising a transposon containing the expression cassette SV40/GFP. A replication competent product virus, ColoAd1/PL30, with a potency equivalent to parental ColoAd1, was identified and the original expression cassette replaced with a TK/TK expression cassette, i.e. a thymidine kinase gene driven by a thymidine kinase promoter, in a manner similar to that describe in Example 5.

Human umbilical vein endothelial cells (HuVEC) and human epithelial lung carcinoma (A549) cells were obtained from ATCC. A549 cells were maintained in DMEM with 10% FBS and HuVEC cells were maintained in EGM (includes Basal medium and SingleQuots). For viral infection, A549 cells were grown in DMEM with 2% FBS, 0.1 nM NEAA and 1% penicillin/streptomycin and HuVEC cells were grown in EGM medium. Viruses were quantitated as previously described.

To determine biological activity of the TK protein, the in vitro cytotoxicity of the virus was assayed with and without addition of gancyclovir (GCV), a compound that is converted by thymidine kinase into a triphosphate analog capable of interfering with both cellular and viral replication. Cells were seeded at a density for each cell line that generated a confluent monolayer within 24 hr. These densely seeded cells were allowed to grow for 2 additional days prior to exposure to the ColoAd1/PL30/TK/TK virus. Infections of both cell lines were carried out in quadruplicate with serial three-fold dilutions of the viruses starting at a particle per cell ratio of 100 and ending at a particle per cell ratio of 0.0152. For each cell type, infections were with or without GCV (20 uM, added at 24 hours post infection). Infected cells were incubated at 37° C. for 8 days post infection and cell viability was measured by the MTS assay. Mock-infected cells with or without GCV addition established the 100% survival point for the given assay.

In HuVec cells (see FIG. 6A), there is no difference in cell killing with or without GCV addition at the lower viral dose range (0.0152 vp/cell to 1.23 vp/cell), but at a higher viral dose range (3.7 vp/cell to 100 vp/cell), addition of GCV prevents cell killing when compared to infection alone. This is explained by the fact that at higher viral doses (11, 33 and 100 vp/cell) in the absence of GVC, the level of initial infection is high enough to result in significant killing of cells due to rounds of viral infection and bursting. In the presence of GCV, the thymidine kinase expressed from the TK promoter within the ColoAd1/PL30/TK/TK virus is inhibited and results in death of the infectious centers, which prevents the viral infection and bursting rounds needed for a significant cell kill. In A549 cells, addition of GCV significantly protects against cell killing at all doses of viral infection. The significant killing at all vp/cell (as compared to the HuVEC cells) is due to the fact that the virus replicates much faster in the A549 cells than in HuVec cells, allowing a much greater number of rounds of infection and bursting in the absence of GCV.

All patents and publications and patents mentioned in the above specification are herein incorporated by reference. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A replication competent virus containing a functional insertion site identified by a method comprising steps of:
(a) mixing a plasmid comprising the genomic DNA of a target virus with a plasmid donor DNA comprising a Tn7-based transposon and an origin of replication under conditions that allow transposition wherein the transposon comprises at least one genetic element of interest operably linked to an expression element and a selectable gene and inserts into the target viral genome in a non-biased manner, wherein the genomic DNA of the target virus does not comprise particular sequences on which the Tn7-based transposon depends on for insertion; and
(b) isolating replication competent viruses obtained from step (a) which express the genetic element of interest.

2. The replication competent virus of claim 1 wherein isolation step (b) comprises assaying for expression of the genetic element of interest in animal cells transfected with the replication competent viruses.

3. The replication competent virus of claim 1 wherein the target virus is an animal virus.

4. The replication competent virus of claim 1 wherein the genetic element is a gene which encodes a reporter molecule, a therapeutic protein or an RNA molecule.

5. The replication competent virus of claim 1 wherein the transposon further comprises an expression element wherein the element is located upstream from, and is operably linked to, the genetic element of interest.

6. The replication competent virus of claim 1 wherein the expression element is a eukaryotic promoter or a eukaryotic splice acceptor sequence.

7. The replication competent virus of claim 1 wherein the genetic element is a therapeutic protein.

8. The replication competent virus of claim 1, wherein the method further comprises replicating the virus in a cell.

9. The replication competent virus of claim 1, wherein the genetic element of interest is replaced.

10. A replication competent virus containing a functional insertion site identified by a method comprising steps of:
(a) mixing genomic DNA of a target virus with a donor DNA comprising a Tn7-based transposon under conditions that allow transposition wherein the transposon comprises at least one genetic element of interest and inserts into the viral genome in a non-biased manner, wherein the genomic DNA of the target virus does not comprise particular sequences on which the Tn7-based transposon depends on for insertion; and
(b) isolating replication competent viruses obtained from step (a) which express the genetic element of interest.

11. The replication competent virus of claim 10 wherein the transposon further comprises a selectable gene.

12. The replication competent virus of claim 10, wherein the method further comprises replicating the virus in a cell.

13. The replication competent virus of claim 10, wherein the genetic element of interest is replaced.

14. A replication competent virus containing a functional insertion site identified by a method comprising steps of:
(a) mixing a plasmid comprising the genomic DNA of an Ad5 virus with a plasmid donor DNA comprising a Tn7-based transposon and an R6K origin of replication under conditions that allow transposition wherein the transposon comprises a gene encoding GFP operably linked to an expression element and a chloramphenicol resistance gene, wherein the transposon inserts into the genomic DNA of the Ad5 virus in a non-biased manner, and wherein the genomic DNA of the Ad5 virus does not comprise particular sequences on which the Tn7-based transposon depends on for insertion; and
(b) isolating replication competent Ad5 viruses which express GFP obtained from step (a).

15. The replication competent virus of claim 14, wherein the method further comprises replicating the virus in a cell.

* * * * *